United States Patent [19]

Ehr et al.

[11] Patent Number: 5,242,568
[45] Date of Patent: Sep. 7, 1993

[54] ELECTROPHORESIS APPARATUS

[75] Inventors: Timothy G. J. Ehr, Menomonee Falls; Stephen H. Gorski, Wauwatosa; Richard K. Vitek, Brookfield, all of Wis.

[73] Assignee: Fotodyne Incorporated, New Berlin, Wis.

[21] Appl. No.: 820,558

[22] Filed: Jan. 14, 1992

[51] Int. Cl.$^5$ .................. G01N 27/26; G01N 27/447; B01D 57/02
[52] U.S. Cl. .............................. 204/299 R; 204/182.8
[58] Field of Search .................... 204/299 R, 182.8

[56] References Cited

U.S. PATENT DOCUMENTS

| | | | |
|---|---|---|---|
| 3,047,489 | 7/1962 | Raymond | 204/182.8 X |
| 3,751,357 | 8/1973 | Rains | 204/182.8 X |
| 3,819,505 | 6/1974 | Parent et al. | 204/299 R |
| 3,888,759 | 6/1975 | Elson et al. | 204/182.8 X |
| 4,061,561 | 12/1977 | Fletcher et al. | 204/299 R |
| 4,130,471 | 12/1978 | Grunbaum | 204/299 R X |
| 4,151,065 | 4/1979 | Kaplan et al. | 204/182.8 X |
| 4,385,974 | 5/1983 | Shevitz | 204/299 R |
| 4,588,491 | 5/1986 | Kreisher et al. | 204/299 R |
| 4,608,146 | 8/1986 | Penaluna | 204/299 R |
| 4,657,655 | 4/1987 | Smoot et al. | 204/299 R |
| 4,830,725 | 5/1989 | Berninger et al. | 204/299 R |
| 5,137,613 | 11/1992 | Brumley, Jr. et al. | 204/299 R |

OTHER PUBLICATIONS

Robert L. Brumley, Jr. and Lloyd M. Smith, "Rapid DNA sequencing by horizontal ultrathin gel electrophoresis" Nucleic Acids Research, vol. 19, No. 15 (1991) 4121–4126.

Primary Examiner—John Niebling
Assistant Examiner—John S. Starsiak, Jr.
Attorney, Agent, or Firm—Michael, Best & Friedrich

[57] ABSTRACT

Electrophoresis apparatus comprising a base including a water jacket, a generally horizontal bottom plate having an upper surface, and a lower surface which is supported by the base and which extends over the water jacket, an endless gasket having a lower surface engaging the upper surface of the bottom plate, and having an upper surface, and a generally horizontal top plate having a lower surface seated on the upper surface of the gasket so as to define between the plates and inside the gasket a space adapted to contain a separation medium.

49 Claims, 11 Drawing Sheets

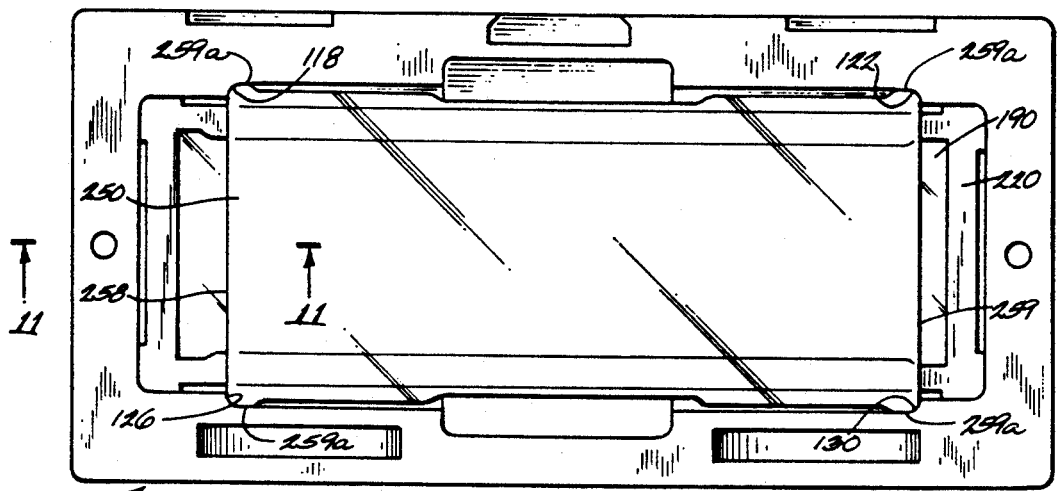
Fig. 10
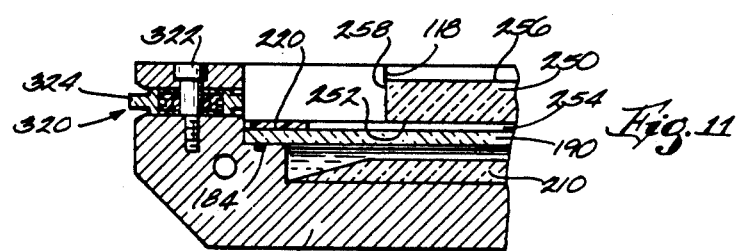
Fig. 12
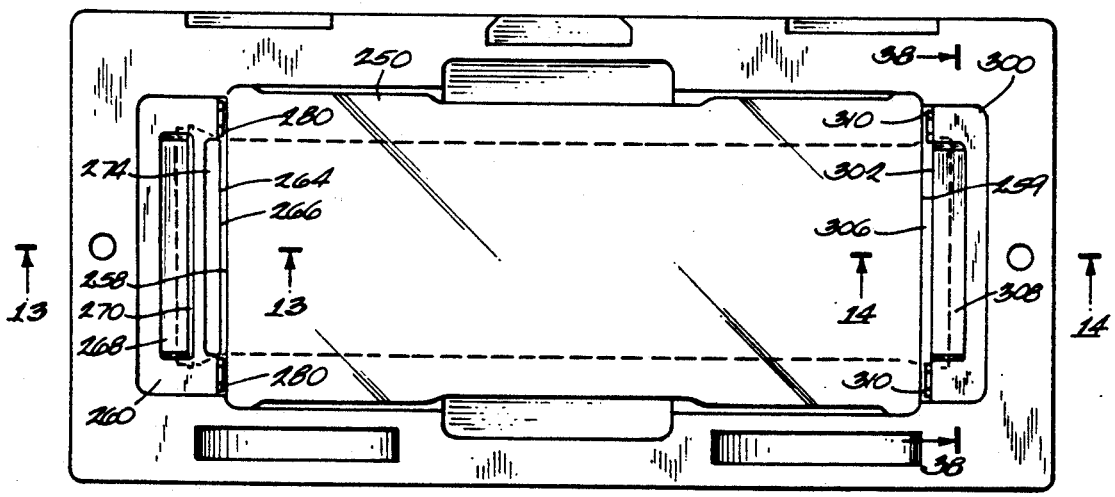
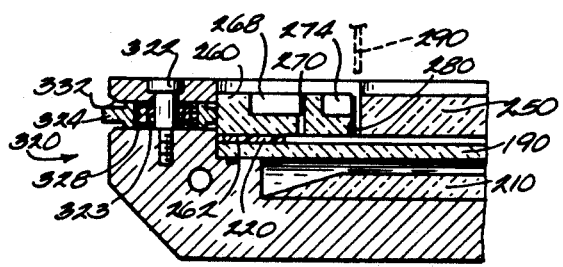
Fig. 13
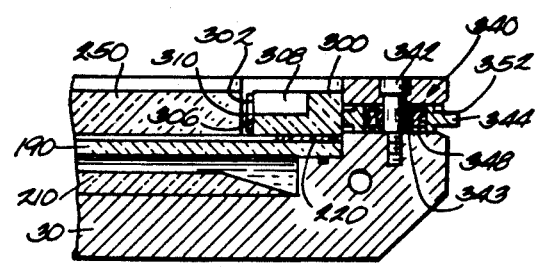
Fig. 14

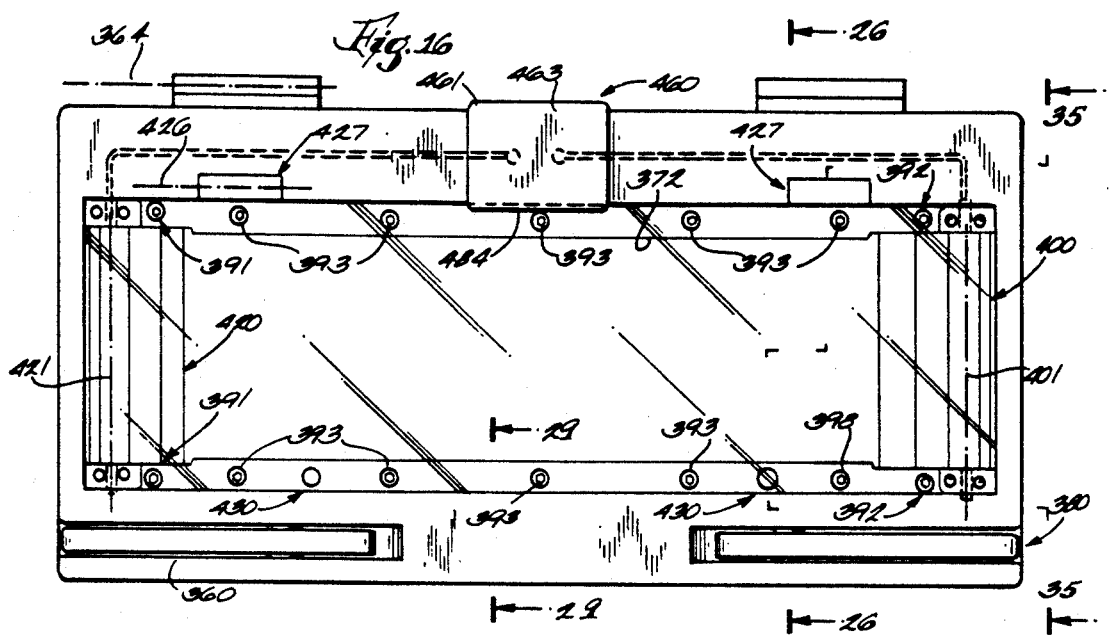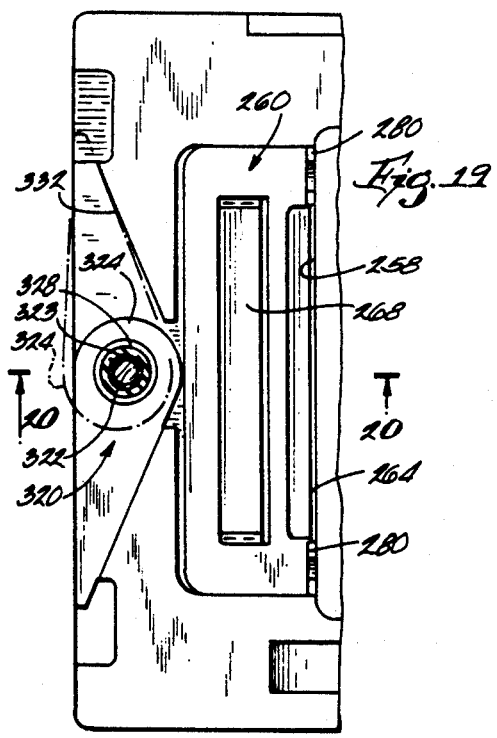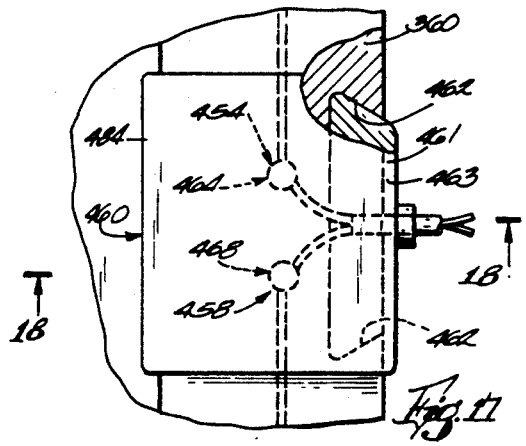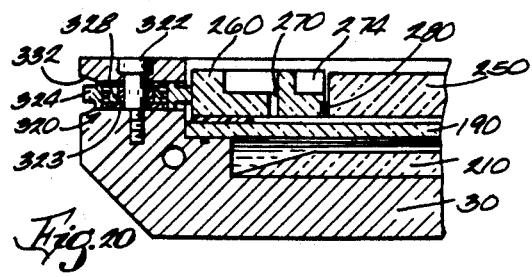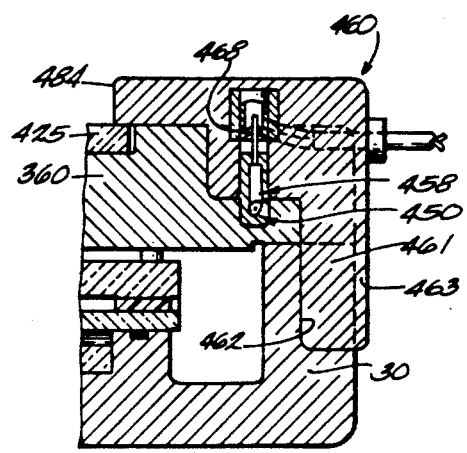

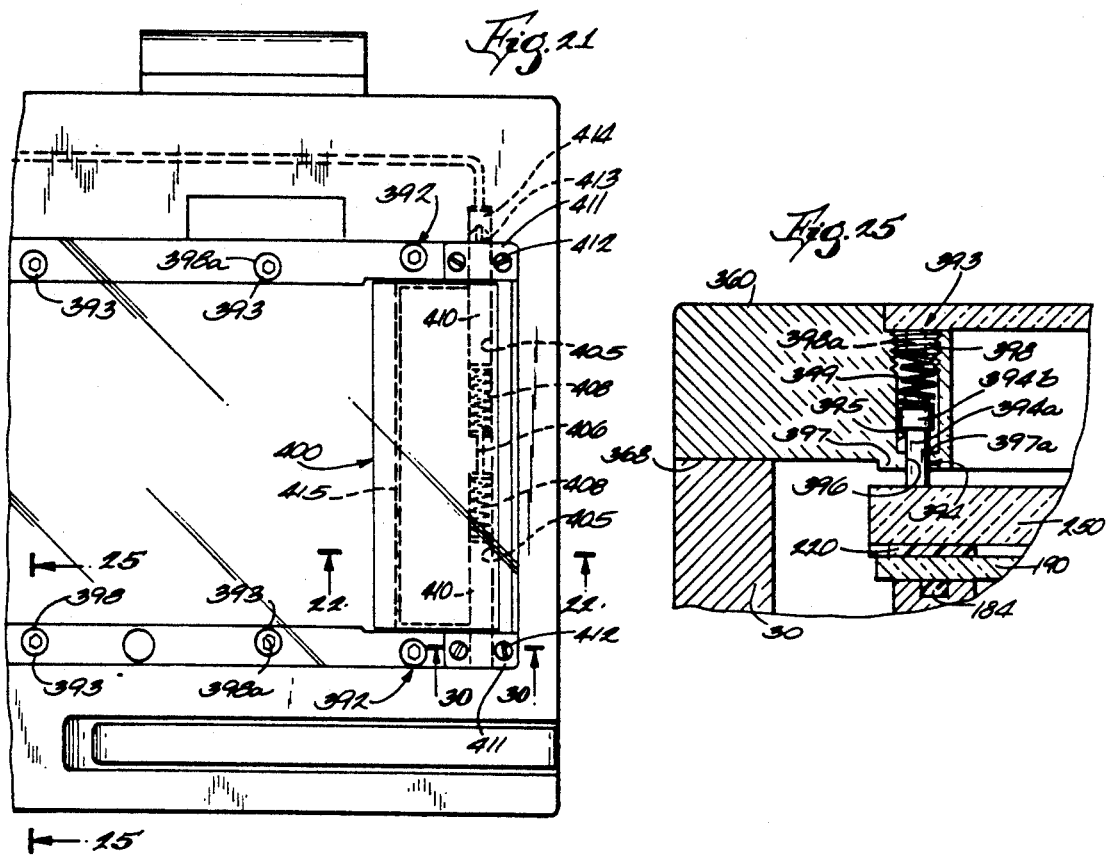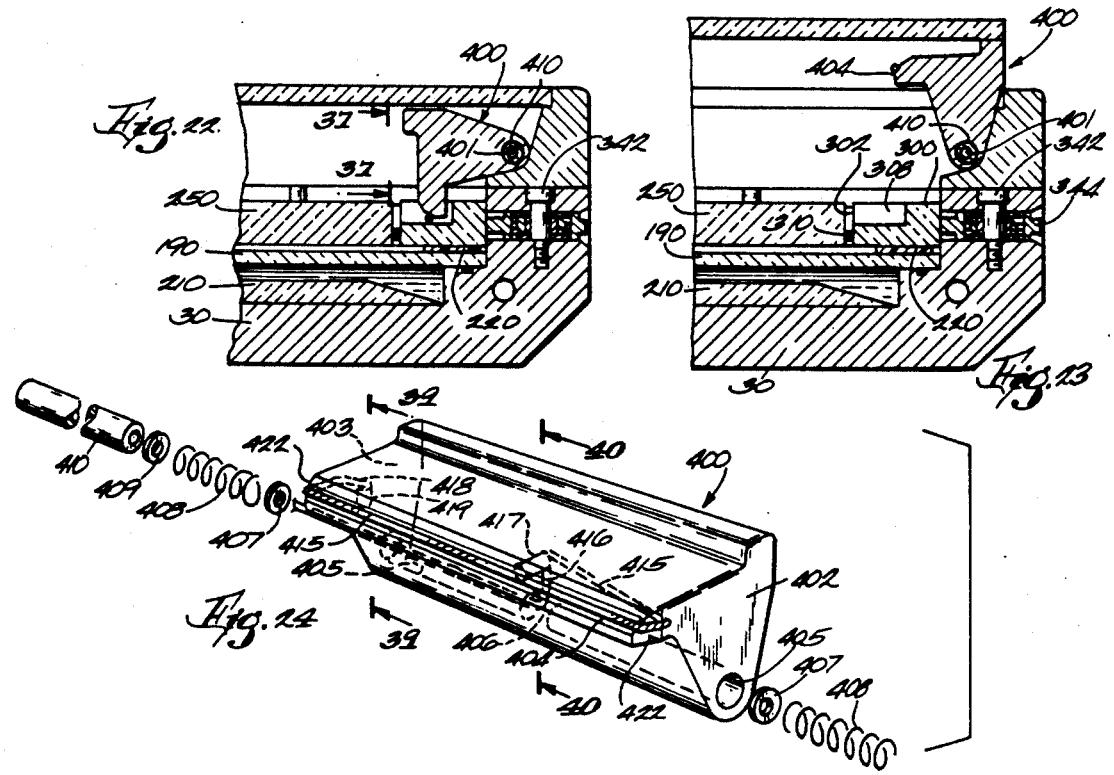

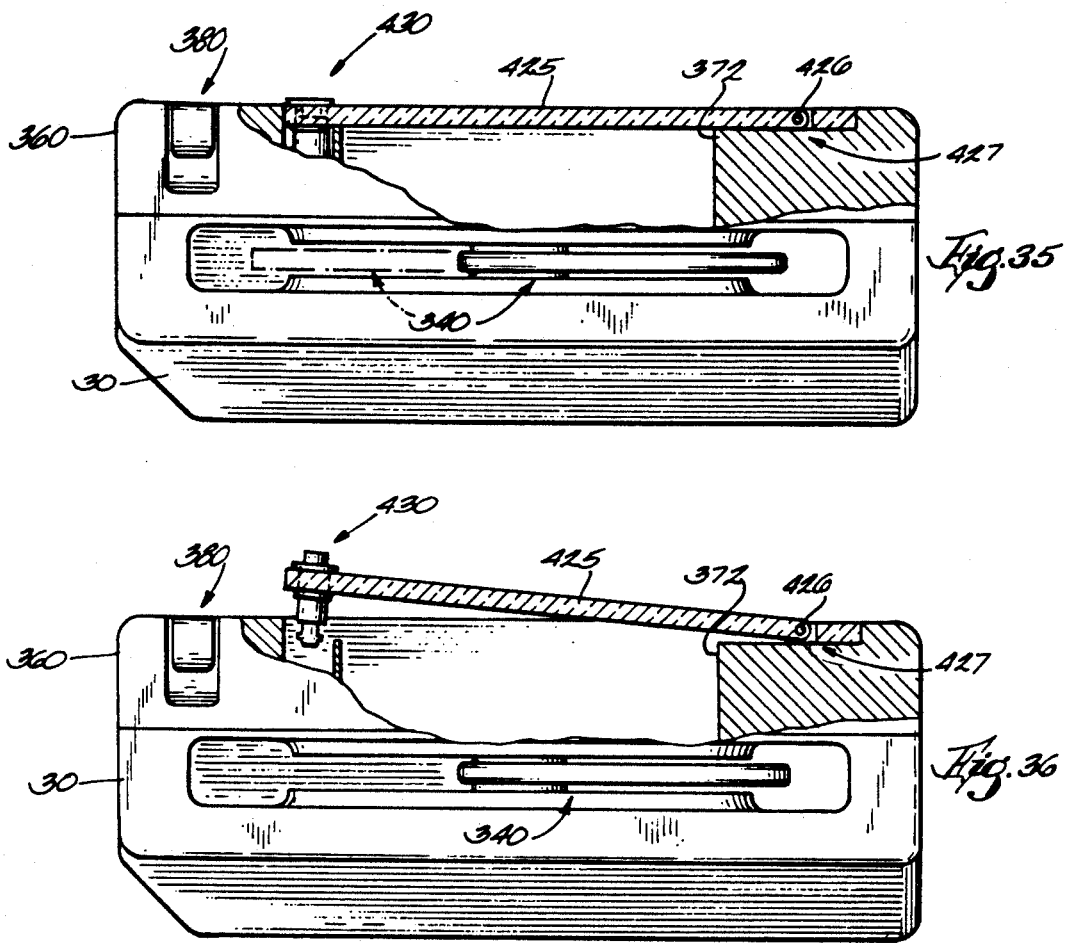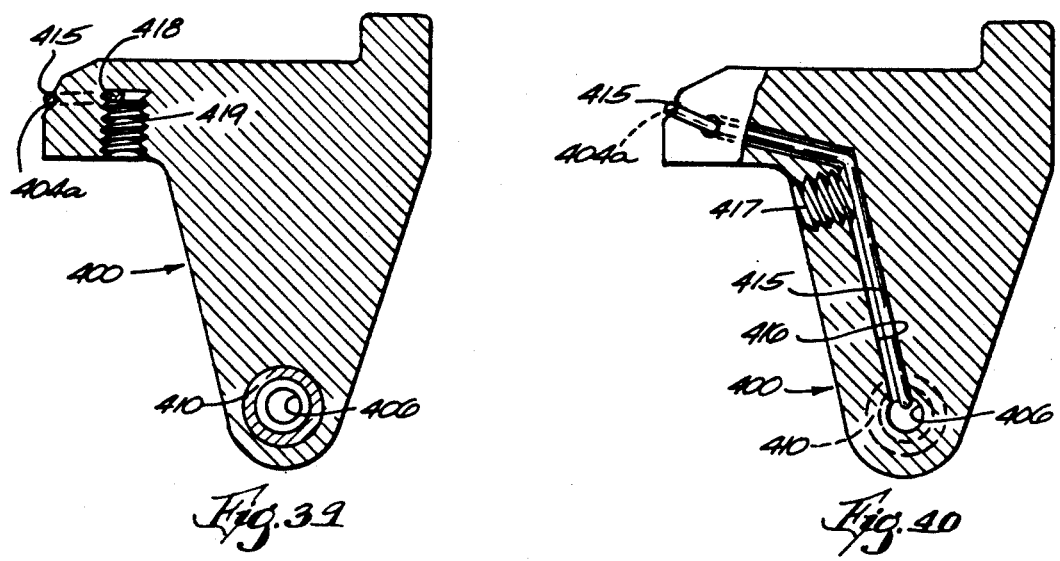

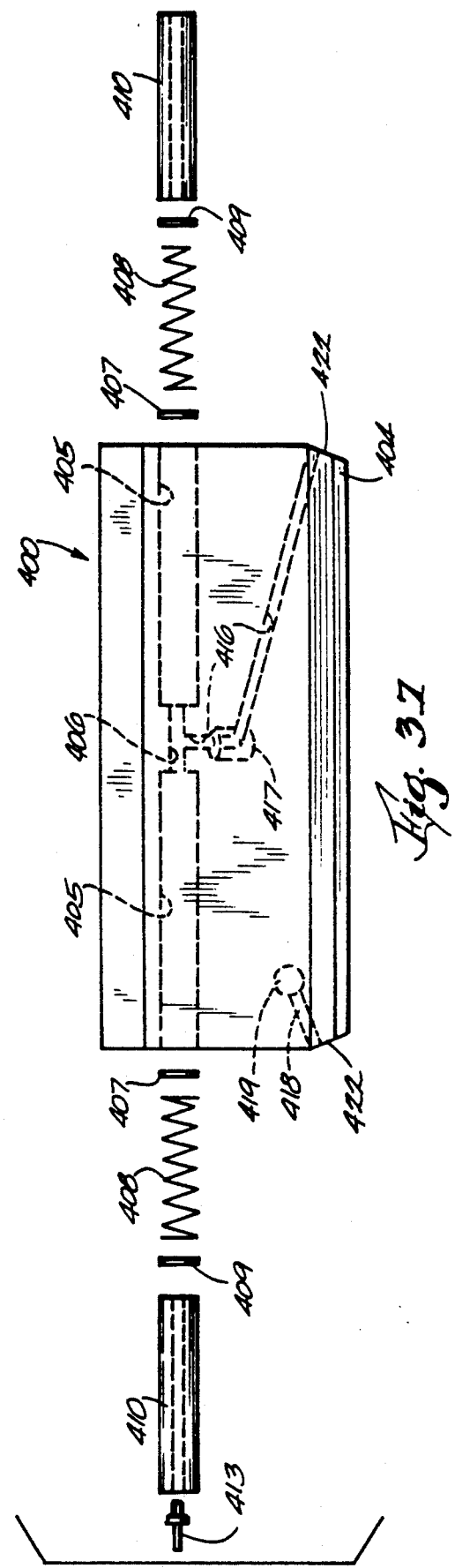

ELECTROPHORESIS APPARATUS

FIELD OF THE INVENTION

The invention relates to apparatus used in gel electrophoretic separations of DNA molecules, protein and other charged molecules. This is commonly referred to as DNA sequencing apparatus or electrophoresis apparatus.

BACKGROUND OF THE INVENTION

In general, such sequencing apparatus consists of a separation media, typically polyacrylamide gel, constrained between glass plates. Prepared DNA samples are introduced into one end of the gel. Each end of the gel is coupled to a high voltage electrode by means of an electrolyte buffer solution. A high voltage electric field is applied to the gel, causing the DNA molecules to migrate in relation to their size. The DNA is not readily detectable alone, and the samples are typically labeled with radioactive or fluorescent dyes, enabling secondary detection through autoradiographic film or optical sensing.

Conventional sequencing gels are operated with the gels placed vertically. This does not facilitate good heat transfer in the gel medium, and limitations are imposed to the amount of power that can be dissipated from the gel or by the cell. This power limitation also limits the strength of the electric field that can be applied to the gel, and hence it limits the speed with which the separation can be performed. Conventional separations take 2 to 8 hours and typically have a gel thickness of 0.2 to 3 mm. This makes possible a thermal gradient upon the gel, which gradient can limit the resolution of the migrating molecules since this migration is temperature dependent.

A U.S. Patent application filed Dec. 20, 1990 and titled "Horizontal Gel Electrophoresis Apparatus," is licensed to the assignee hereof and is incorporated herein by reference. This application discloses a device, hereinafter referred to as the "Brumley/Smith Apparatus," which improves upon prior art by its horizontal water cooled layout and ultrathin slab gel (approximately 60 microns typical). These features facilitate improved speed and resolution by allowing efficient heat transfer and minimizing thermal gradients across the gel material. Much higher electric fields across the gel are possible, resulting in reduced time to separate. A typical duration is 15-20 minutes.

SUMMARY OF THE INVENTION

The Brumley/Smith Apparatus can be difficult to implement. The placement of the top glass, sample chamber piece, and buffer chamber piece are regulated by screw clamps which leave considerable variability in compression open to the user. This lack of constraint requires considerable education to correctly employ the proper clamp pressure. Under-tightening the screws can cause leakage, which puts potentially lethal voltages in proximity to water. Overtightening the screws can cause the glass pieces to break. The Brumley/Smith Apparatus provides uneven heat transfer between the water and the gel because of the water inlet construction and the water jacket shape. There are no interlocks to protect the user from exposure to the high voltage potentials present at the periphery of the glass or the buffer chambers. Another possible source of leakage current is the formation of crystalline material, particularly urea, around the periphery of the gel as it migrates past the gel spacer. This can disrupt the applied electric field to the gel.

The present invention provides augmentations to the original Brumley/Smith apparatus. These augmentations greatly increase its usability and safety, and solve many of the engineering tolerance problems associated with practical manufacture. The invention also provides a system of components to support the operation of the cell, including: (1) a unit to provide temperature regulation of the water circulated through the cell, (2) a source of high voltage to bias the gel, and (3) a device to dry the gel after the separation has been performed.

The present invention is a device for forming thin slab gels for separation of charged molecules, such as DNA and proteins, by electrophoresis. The device consists of a cell with proteins, by electrophoresis. The device consists of a cell with a hinged base and cover, and a system of components to support the operation of the cell.

The cell base has integral to it a path for water circulation, a recess in which the bottom plate can be held against an O-ring seal, and seats for cams which perform the operation of compression of the top glass pieces. Because leakage, if it happens for any reason, presents an electrical hazard when combined with the high voltage power source, the base also includes wells that confine water in the event of leakage. The wells are defined in part by walls that limit the travel of the top glass plate, preventing the distortion of the gel spacer beneath it. The base also contains finger wells on either side of the plates which allow the operator to insert and remove the plates at a location where the radioactivity is at a minimum. The arrangement of the base and the top plate necessitate proper placement of the anode and cathode blocks.

The end compression cams provide controlled force to bring the three top pieces together. This action eliminates the uncertainties associated with the Brumley/Smith Apparatus end clamps.

Another feature of the invention is the design of a gel spacer which is indented from the periphery of the glass plates to which it is applied. This minimizes the migration of urea crystals at the glass plate periphery experienced in the Brumley/Smith Apparatus.

The cell cover has integral to it several spring loaded plunger clamps which provide controlled pressure to hold the glass plates in place. This solves the problem experienced in the Brumley/Smith Apparatus with clamp variability. Latch members secure the cover in its closed posion and also provide support for the cover when the cover is in its open position. The cover has therein an opening affording access to the inside of the cell, and an access lid pivotally mounted on the cover opens and closes the access opening.

Additionally, the cover contains the high voltage electrodes and a connector to attach these electrodes to a high voltage power supply. Chamfers on the electrodes and on the anode and cathode blocks guide the electrodes into the respective buffer chambers. There is an interlock present in the design of the high voltage connector, the cover and the access lid such that the connector cannot be applied to the unit when either the cover or the access lid is open. The interlock also prevents opening of either the cover or the access lid when the connector is engaged. It is the object of the inven-

DESCRIPTION OF THE DRAWINGS

FIG. 10 is a top plan view of the base with the water jacket insert, the bottom plate, the gasket and the top plate mounted thereon.

FIG. 11 is a view taken along line 11—11 in FIG. 10.

FIG. 12 is a top plan view of the base with the water jacket insert, the bottom plate, the gasket, the top plate, the cathode block and the anode block mounted thereon.

FIG. 13 is a view taken along line 11—13 in FIG. 12.

FIG. 14 is a view taken along line 14—14 in FIG. 12.

FIG. 16 is a top plan view of the sequencing cell.

FIG. 17 is an enlarged portion of the top plan view, turned 90 degrees and partially cut away.

FIG. 18 is a view taken along line 18—18 in FIG. 17.

FIG. 19 is an enlarged portion of the top plan view, partially cut away.

FIG. 20 is a view taken along line 20—20 in FIG. 19.

FIG. 21 is an enlarged right end portion of the top plan view.

FIG. 22 is a view taken along line 22—22 in FIG. 21.

FIG. 23 is a view similar to FIG. 22 showing the anode electrode in its up position.

FIG. 24 is a perspective view of the anode electrode.

FIG. 25 is a view taken along line 25—25 in FIG. 21.

FIG. 35 is a view taken along line 35—35 in FIG. 16.

FIG. 36 is a view similar to FIG. 35 showing the lid in its open position.

FIG. 37 is an exploded view taken along line 37—37 in FIG. 22.

FIG. 39 is a view taken along line 39—39 in FIG. 24.

FIG. 40 is a view taken along line 40—40 in FIG. 24.

Figure 1:
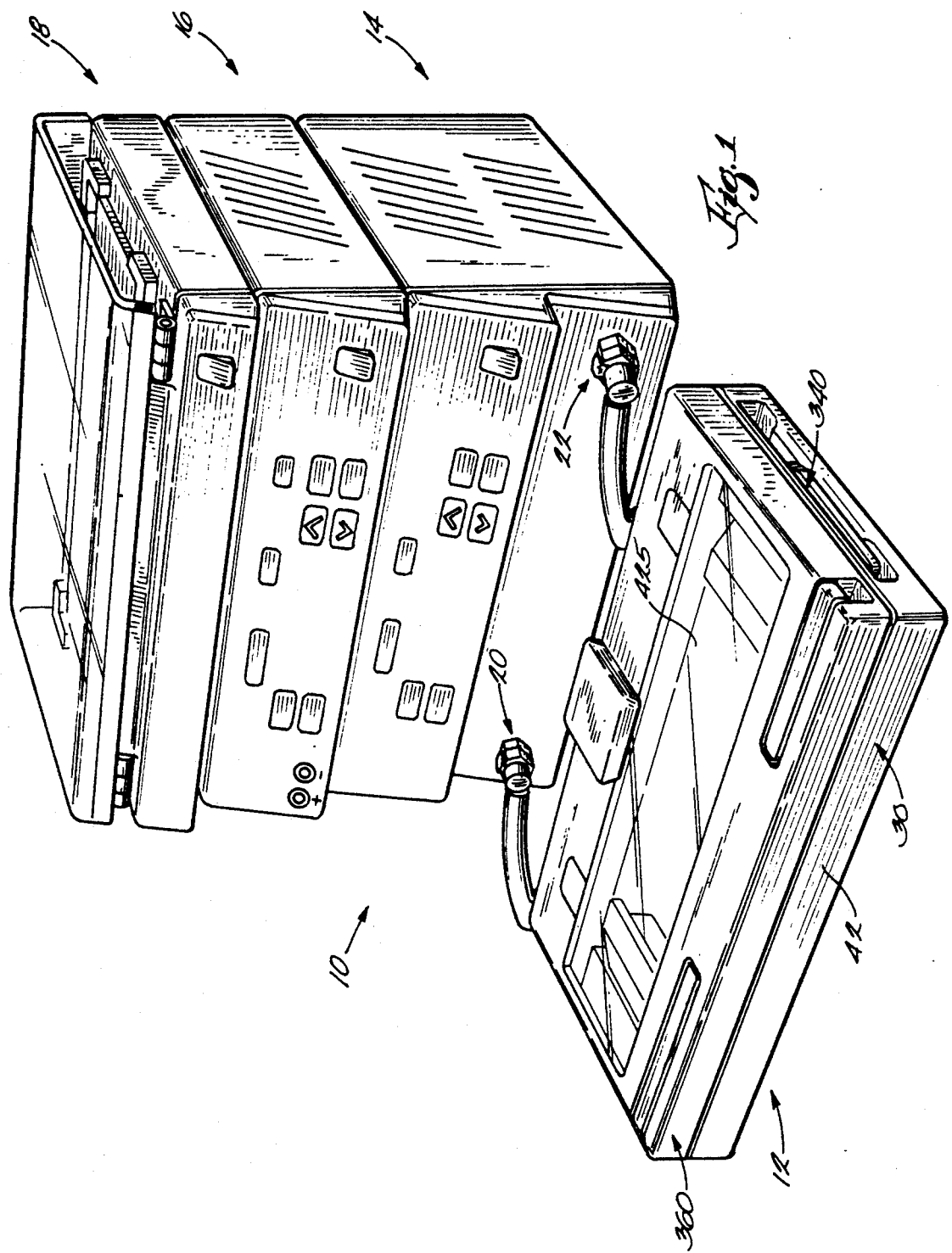
FIG. 1 is a perspective view of apparatus embodying the invention and comprising a sequencing cell, a temperature regulator, a power supply, and a gel dryer.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

An electrophoresis apparatus 10 embodying the invention is illustrated in the drawings. As shown in FIG. 1, the apparatus 10 comprises, generally, a sequencing cell 12, a fluid circulator and temperature regulator 14, a power supply 16, and a gel dryer 18. The power supply 16 and gel dryer 18 are conventional and will not be described in greater detail. The fluid circulator and temperature regulator 14 has a water outlet 20 and a water inlet 22 and provides, as described below, water having a controlled temperature to the sequencing cell 12. The fluid circulator and temperature regulator is preferably the same as is described in copending Application Ser. No. 07/820,529, which is titled "Fluid Circulator and Temperature Regulator," which was filed concurrently herewith, which is assigned to the assignee hereof, and which is incorporated herein by reference.

Figure 2:
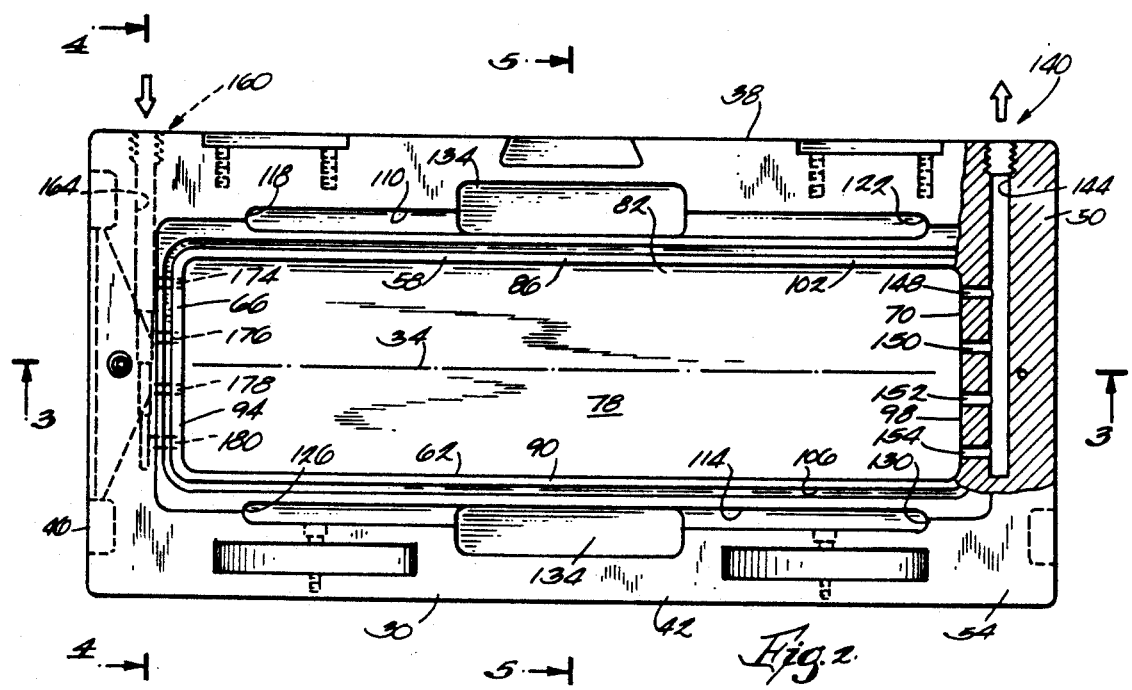
FIG. 2 is a top plan view of the base of the sequencing cell.

The sequencing cell 12 comprises a generally rectangular base 30. The base is preferably made of plastic and has (see FIG. 2) a longitudinal axis 34, opposite first and second (rear and front, as shown in FIG. 1) sides 38 and 42 parallel to the axis 34, and opposite first and second (left and right, as shown in FIG. 2) ends 46 and 50 spaced along the axis 34. The base 30 includes a generally horizontal upper surface 54. Opposite side walls 58 and 62, opposite end walls 66 and 70 and a generally horizontal bottom wall 74 define a water jacket recess or cavity 78. The water jacket recess 78 partially defines (see FIG. 7) a generally rectangular water jacket 82 having (see FIG. 2) opposite sides 86 and 90 spaced inwardly of the base sides 38 and 42 and opposite upstream and downstream or left and right ends 94 and 98 spaced inwardly of the base ends 46 and 50.

Figure 3:
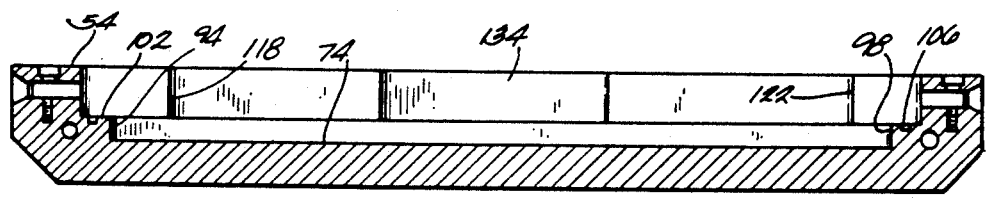
FIG. 3 is a view along line 3—3 in FIG. 2.

The base 30 also includes (see FIGS. 2 and 3) an upwardly facing plate seating surface 102 which surrounds the water jacket 82 and which is recessed below the base upper surface 54. The surface 102 has therein an endless O-ring channel 106. The surface 102 also has therein (see FIG. 2) an elongated well 110 extending along and parallel to the rear side 86 of the water jacket 82 in spaced relation thereto, with the O-ring channel 106 located between the well 110 and the water jacket 82, and an elongated well 114 extending along and parallel to the front side 90 of the water jacket 82 in spaced relation thereto, with the O-ring channel 106 located between the well 114 and the water jacket 82. Vertically extending end walls 118 and 122 define the opposite ends of the well 110, and vertically extending end walls 126 and 130 define the opposite ends of the well 114. The end walls 118, 122, 126 and 130 extend in part above the plate seating surface 102. The base 30 also includes, on opposite sides of the water jacket 82, finger recesses 134 which partially overlap the wells 110 and 114 and which facilitate insertion and removal of the below-described components of the sequencing cell 12.

As shown in FIG. 2, water outlet means 140 extend from the downstream end 98 of the water jacket 82 to the rear side 38 of the base 30. The water outlet means 140 includes a main water outlet passage 144 extending from the rear side 38 of the base 30 in perpendicular relation thereto and in spaced parallel relation to the downstream end 98 of the water jacket 82. The water outlet means 140 also includes four passageways 148, 150, 152 and 154 extending between the main passage 144 and the water jacket 82 in parallel relation to the axis 34. The passageways 148, 150, 152 and 154 have substantially equal cross-sectional areas and are equidistantly spaced, with the distance between each of the front and rear passageways 148 and 154 and the adjacent wall 58 or 62 being ½ of the distance between the passageways 148, 150, 152 and 154. This arrangement of the passageways minimizes turbulence in the water jacket 82.

Figure 4:
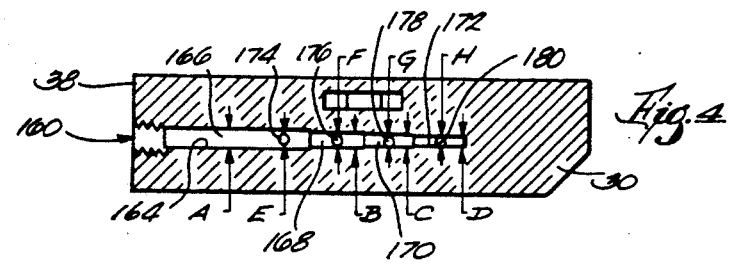
FIG. 4 is a view taken along line 4—4 in FIG. 2.
Figure 5:
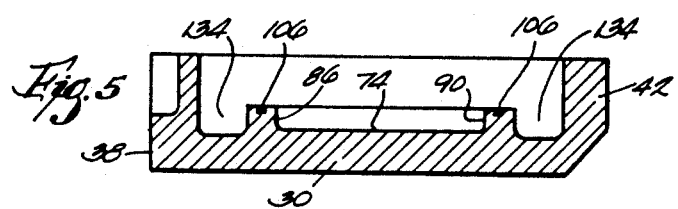
FIG. 5 is a view taken along line 5—5 in FIG. 2.

The base 30 also includes (see FIGS. 2 and 4) water inlet means 160 extending from the rear side 38 of the base 30 to the upstream end 94 of the water jacket 82. The water inlet means 160 includes a main water inlet passage 164 extending from the rear side 38 of the base 30 in perpendicular relation thereto and in spaced parallel relation to the upstream end 94 of the water jacket 82. The main passage 164 includes (see FIG. 4) a first or upstream portion 166 extending from the rear side 38 of the base 30 and having a first cross-sectional area A, a second portion 168 which is downstream of the first portion 166 and which has a second cross-sectional area B, a third portion 170 which is downstream of the second portion 168 and which has a third cross-sectional area C, and a fourth or downstream portion 172 which is downstream of the third portion 170 and which has a fourth cross-sectional area D. The water inlet means 160 also includes a first passageway 174 extending between the first portion 166 and the water jacket 82 and having a fifth cross-sectional area E, a second passageway 176 extending between the second portion 168 and the water jacket 82 and having a sixth cross-sectional area F, a third passageway 178 extending between the third portion 170 and the water jacket 82 and having a seventh cross-sectional area G, and a fourth passageway 180 extending between the fourth portion 172 and the water jacket 82 and having a eighth cross-sectional area H. Each of the passageways 174, 176, 178 and 180 extends in parallel relation to the base axis 34. In the illustrated embodiment, the cross-sectional areas A, B, C, D, E, F, G and H are 0.313 inch, 0.266 inch, 0.228 inch, 0.209 inch, 0.175 inch, 0.221 inch, 0.228 inch, and 0.191 inch, respectively. This inlet arrangement substantially equalizes the water flow out of the four passageways 174, 176, 178 and 180 and into the water jacket 82 and thereby reduces turbulence in the water jacket 82.

Figure 6:
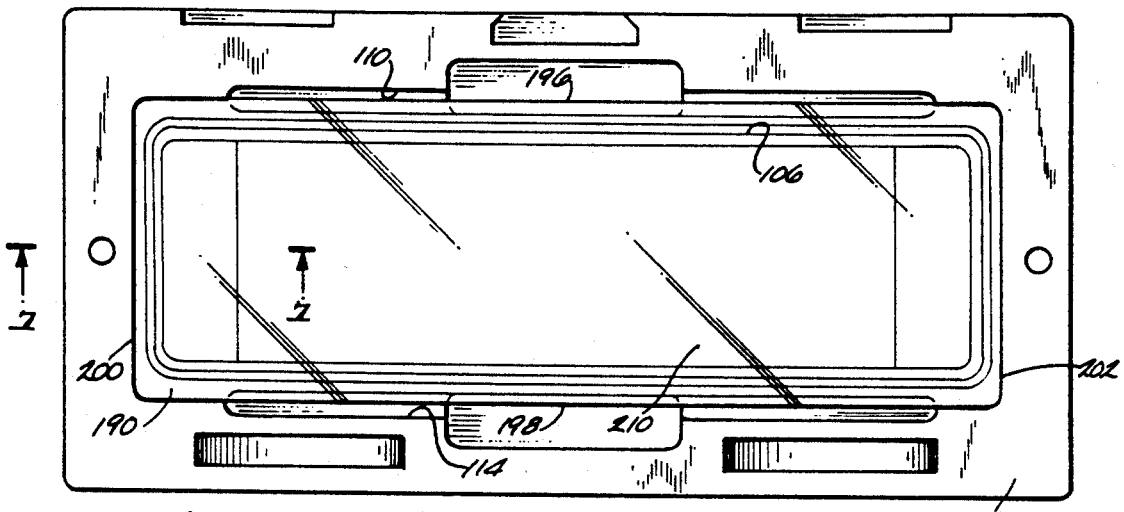
FIG. 6 is a top plan view of the base with the water jacket insert and the bottom plate mounted thereon.

The cell 12 further comprises (see FIG. 7) an O-ring 184 located in the O-ring channel 106, and a generally horizontal bottom or inner plate 190 having an inner or lower surface 192 seated on the O-ring 184. The plate 190 extends over the water jacket recess 78 and partially defines the water jacket 82. The plate 190 has (see FIGS. 6 and 7) an upper or outer surface 194, opposite sides 196 and 198, located above the wells 110 and 114, respectively, and opposite left and right vertical end surfaces 200 and 202 respectively adjacent the ends 94 and 98 of the water jacket 82. The plate 190 is preferably made of tempered glass polished to two-wave flatness. Because the sides of the bottom plate 190 are located over the wells 110 and 114, and the wells 110 and 114 extend inwardly of the sides 196 and 198 of the bottom plate 190, any water leaking past the O-ring 106 will flow into the wells 110 and 114 before reaching the sides 196 and 198 of the bottom plate 190. This reduces the chance of current flow from the below-described gel space to the water jacket 82.

Figure 7:
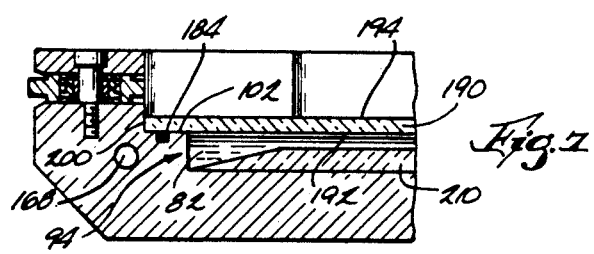
FIG. 7 is a view taken along line 7—7 in FIG. 6.

In the illustrated embodiment (see FIGS. 6 and 7), the sequencing cell 12 also comprises a plate-like insert 210 located in the water jacket cavity 78. The insert is preferably made of plastic. As shown in FIG. 7, the insert 210 is tapered or ramped adjacent the upstream and downstream ends 94 and 98 of the water jacket 82, thereby providing the water jacket 82 with a decreased cross-sectional area at a point downstream of its upstream end 94. This decreased cross-sectional area increases water flow velocity through the water jacket 82 and thereby increases heat transfer between the water jacket 82 and the bottom plate 190. Preferably, the water jacket 82 has a height of 0.375 inch, and the insert has a height of 0.250 inch. The increased cross-sectional areas adjacent the upstream and downstream ends 94 and 98 of the water jacket 82 reduce turbulence at the inlets and outlets.

Figure 8:
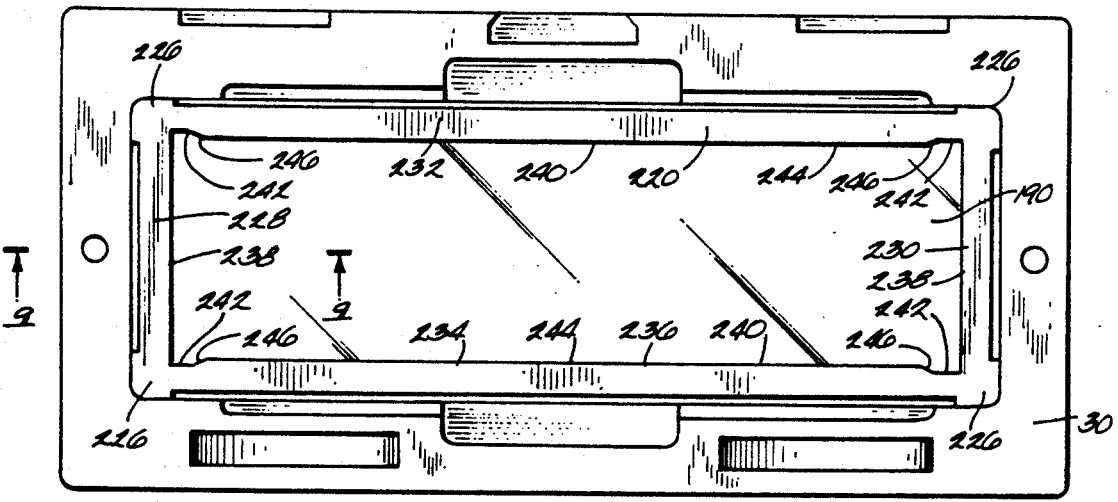
FIG. 8 is a top plan view of the base with the water jacket insert, the bottom plate, and the gasket mounted thereon.
Figure 9:
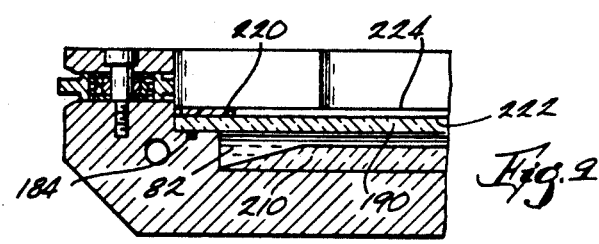
FIG. 9 is a view taken along line 9—9 in FIG. 8.

The sequencing cell 12 also comprises (see FIGS. 8 and 9) an endless, generally rectangular gasket 220. The gasket 220 is made of inert flexible material, preferably polyester, and is disposable. The gasket thickness is preferably 0.002 inch, but can be greater or less if desired. The gasket 220 has (see FIG. 9) a lower surface 222 engaging the upper surface 194 of the bottom plate 190, and has an upper surface 224. The gasket has (see FIG. 8) corner segments 226 aligned with the corners of the bottom plate 190. The gasket 220 also has opposite end segments 228 and 230 located adjacent and spaced inwardly from the opposite ends of the bottom plate 190, and opposite side segments 232 and 234 located adjacent and spaced inwardly from the opposite sides of the bottom plate 190. The gasket 220 thus has side and end portions spaced inwardly from the periphery of the bottom plate. The spaces between the gasket 220 and the periphery of the bottom plate 190 provide room for urea crystals that may result from urea leaking past the gasket 220. This also reduces the likelihood of electrical current flow from the gel space to the water jacket 82.

The gasket 220 further has a generally rectangular inner surface 236 extending between the upper and lower surfaces 224 and 222. The inner surface 236 includes opposite end portions 238 and opposite side portions 240 extending between the end portions 238. Each of the side portions 240 includes an indentation 242 adjacent each of the end portions 238. Stated alternatively, each of the side segments 232 and 234 includes an interior surface, which interior surface has therein an indentation 242 adjacent each of the end segments 228 and 230 and includes a generally linear main portion 244 and a ramped transition 246 between each of the indentations 242 and the main portion 244. The indentations 242 in the inner surface of the gasket 220 permit the below-described electrodes to be slightly wider than the majority of the gel space. The ramped transitions condense and "linearize" the electric field in the gel space.

The sequencing cell 12 also comprises (see FIGS. 10 and 11) a generally horizontal top plate 250 having a lower or inner surface 252 seated on the upper surface 224 of the gasket 220. The lower surface 252 of the top plate 250 cooperates with the upper surface 194 of the bottom plate 190 and the inner surface 236 of the gasket 220 to define (see FIG. 11) a space 254 adapted to contain a separation medium such as a polyacrylamide gel. This space 254, which is referred to herein as the "gel space," is further defined by the lower surfaces of the below-described cathode and anode blocks.

The top plate 250 also has an upper or outer surface 256 and opposite vertical end surfaces 258 and 259 engaged by the vertical walls 118, 122, 126 and 130 of the base 30 so that the walls limit movement of the top plate 250 axially of the base. The top plate 250 has a length substantially less than the length of the gasket 220 such that the ends of the top plate 250 are spaced inwardly of the ends of the gasket 220. The top plate 250 also has opposite vertical side surfaces having portions 259a engaged by the side walls of the wells 110 and 114 so as to limit lateral movement of the top plate 250. The top plate 250 is preferably made of tempered glass polished to two-wave flatness.

The sequencing cell 12 further comprises (see FIGS. 12 and 13) a cathode block 260 which is located adjacent the left end surface 258 of the top plate 250 and which has a substantrally planar lower surface 262 seated on the upper surface 224 of the gasket 220. The cathode block 260 has a vertical end surface 264 spaced from the end surface 258 of the top plate 250 so as to form therebetween a gap 266 communicating with the gel space 254. The gap 266 is maintained by the below-described cathode gaskets. The end surface 264 has therein, adjacent the opposite ends thereof (i.e., adjacent the side segments 232 and 234 of the gasket 220), U-shaped recesses 267, the reason for which is explained below. The cathode block 260 defines an upwardly opening buffer chamber 268, and the block 260 has therethrough a slot 270 communicating between the buffer chamber 268 and the gel space 254. The cathode block 260 also defines an upwardly opening sample chamber 274 which communicates with the gap 266 and which is located between the buffer chamber 268 and the top plate 250.

Figure 15:
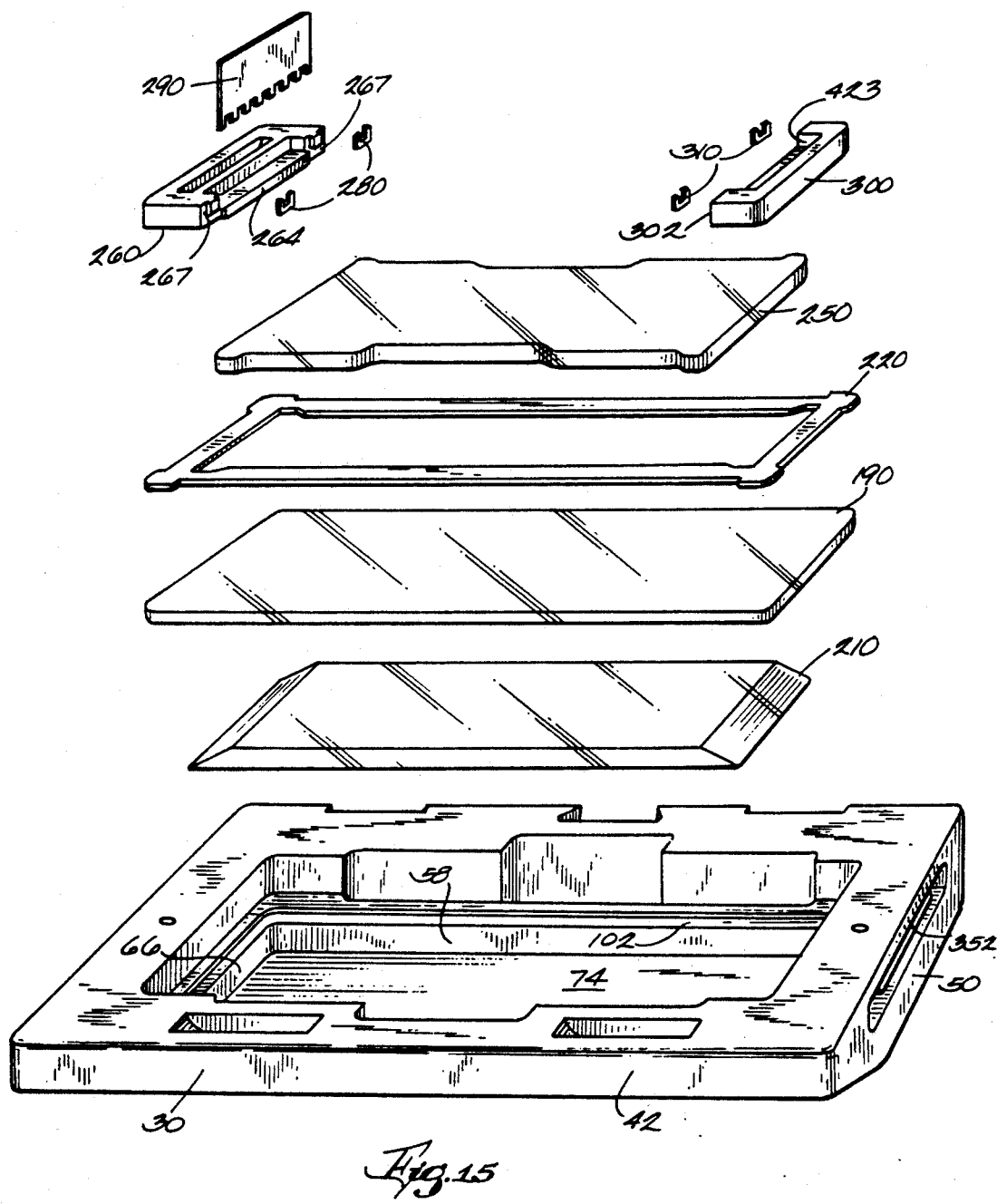
FIG. 15 is an exploded perspective view of the base, the water jacket insert, the bottom plate, the gasket, the top plate, the cathode block, the cathode block gaskets, the anode block, the anode block gaskets and the comb.
Figure 26:
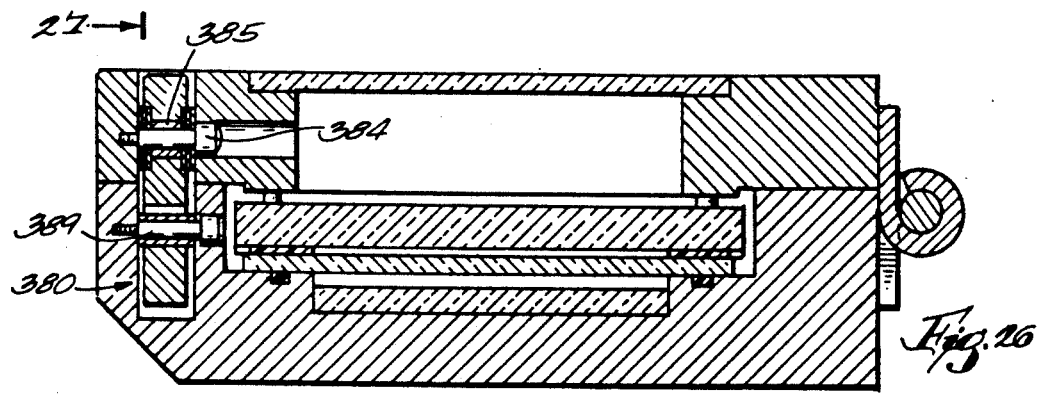
FIG. 26 is a view taken along line 26—26 in FIG. 16.

A pair of cathode gaskets 280 are located in the gap 266. Each gasket 280 is U-shaped, opens upwardly, and is housed in a respective one of the recesses 267 so that each gasket 280 sealingly engages the cathode block end surface 264, the top plate end surface 258 and a respective one of the gasket segments 232 and 234. A conventional comb 290 (see FIG. 15) is located in the gap 266 between the cathode gaskets 280. As is known in the art, the comb 290 extends into the gel space to define sample wells.

The sequencing cell 12 further comprises (see FIGS. 12 and 14) an anode block 300 located adjacent the right end surface 259 of the top plate 250. The anode block 300 has a vertical end surface 302 spaced from the right end surface 259 of the top plate 250 so as to form therebetween a gap 306 communicating with the gel space 254. The anode block 300 defines an upwardly opening buffer chamber 308 communicating with the gap 306.

A pair of anode gaskets 310 are located in the gap 306. Each of the gaskets 310 is U-shaped, opens upwardly, and sealingly engages the anode block end surface 302, the top plate end surface 259, and a respective one of the gasket segments 232 and 234.

The cell 12 further comprises (see FIGS. 13 and 19) cam means 320 for biasing the cathode block end surface 264 toward the top plate end surface 258. The cam means 320 preferably includes a generally vertical pivot pin 322 supported by the base 30, a bearing 323 surrounding the pin 322, a cam member 324 pivotally mounted on the bearing 323, and a resilient bushing 328 between the cam member 324 and the bearing 323. The cam member 324 is housed in a recess 332 in the left end of the base 30 and is movable between a biasing position (shown in solid lines in FIG. 19) and a non-biasing position (shown in phantom in FIG. 19). In the biasing position, the cam member 324 engages the cathode block 260 so as to bias the cathode block 260 toward the top plate 250 (to the right as shown in FIG. 19), whereby the cathode gaskets 280 are compressed between the cathode block 260 and the top plate 250 and the bushing 328 is compressed between the cam member 324 and the bearing 323. In the non-biasing position, the cam member 324 does not exert a force on the cathode block 260.

In the illustrated embodiment, the cathode gaskets 280 are 0.060 inch thick, the recesses 267 in the cathode block end surface 264 are 0.020 inch deep, and the comb 290 is 0.030 inch thick. When the cam member 324 is moved to its biasing position so as to compress the cathode gaskets 280, the gaskets 280 are compressed to a thickness of 0.050 inch, so that the cathode block end surface 264 and the top plate end surface 258 engage the opposite sides of the comb 290. The force exerted on the cathode block 260 by the gaskets 280 is just slightly less than the force exerted on the cathode block 260 by the cam 324, so that the gap 266 does not close when the comb 290 is removed.

As shown in FIG. 14, cam means 340 are also provided for biasing the anode block end surface 302 toward the top plate end surface 259 (to the left as shown in FIG. 35). The cam means 340 includes a generally vertical pivot pin 342 supported by the base 30, a bearing 343 surrounding the pin 342, a cam member 344 pivotally mounted on the bearing 343, and a resilient bushing 348 between the cam member 344 and the bearing 343. The cam member 344 is housed in a recess 352 in the right end of the base 30. The cam member 344 is movable between a biasing position (shown in phantom in FIG. 35) and a non-biasing position (shown in solid lines in FIG. 35). In the biasing position, the cam member 344 engages the anodo block 300 so as to bias the anode block 300 toward the top plate 250, whereby the anode gaskets 310 are compressed between the anode block 300 and the top plate 250, although not enough to close the gap 306, and the bushing 348 is compressed between the cam member 344 and the bearing 343. In the non-biasing position, the cam member 344 does not exert a force on the anode block 300.

Preferably, the force exerted on the cathode block 260 by the cam member 324 is less than the force exerted on the anode block 300 by the cam member 344. As a result, the cam member 344, acting through the anode block 300 and the anode gaskets 310, pushes the left end 258 of the top plate 250 against the base walls 118 and 126, thereby locating the top plate 250 relative to the base 30. The cam member 324, acting through the cathode block 260, pushes the cathode gaskets 280 against the left end 258 of the top plate 250. Because the force exerted by the cam member 344 is greater than the force exerted by the cam member 324, the cam member 324 does not move the left end 258 of the top plate 250 away from the base walls 118 and 126.

The sequencing cell 12 further comprises (see FIGS. 1, 16 and 32) a cover 360 mounted on the base 30 for pivotal movement relative thereto about a generally horizontal axis 364 extending parallel to the base axis 34.

Figure 32:
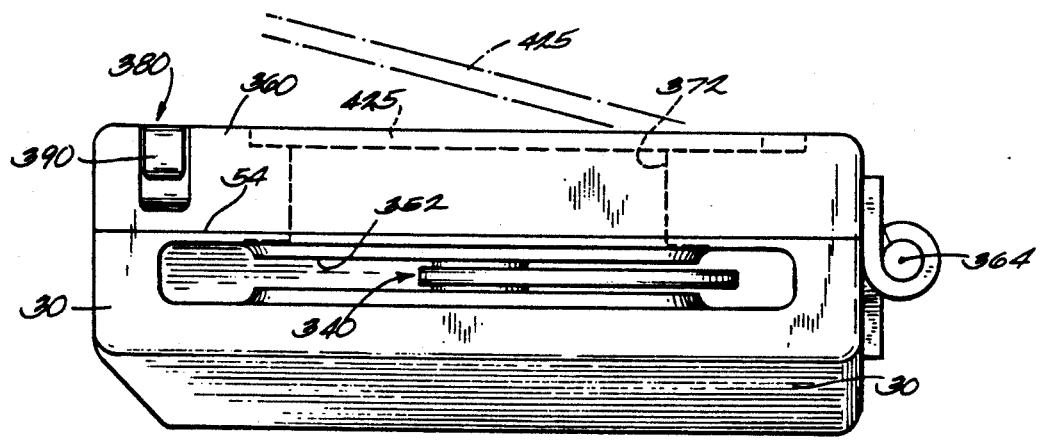
FIG. 32 is a right end elevational view of the sequencing cell as shown in FIG. 16.
Figure 33:
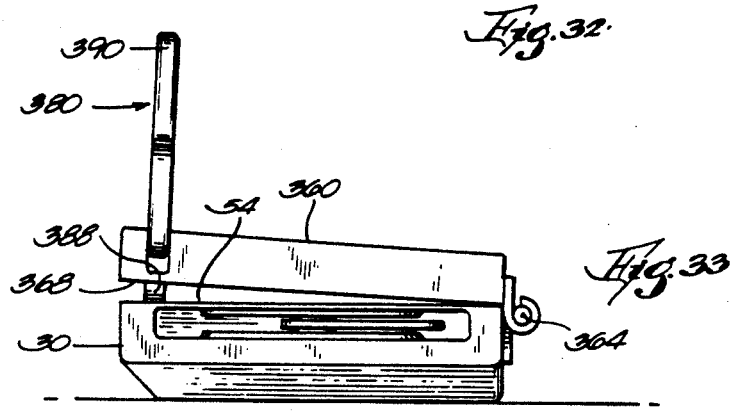
FIG. 33 is a reduced view similar to FIG. 32 showing the latching members in their released positions.
Figure 34:
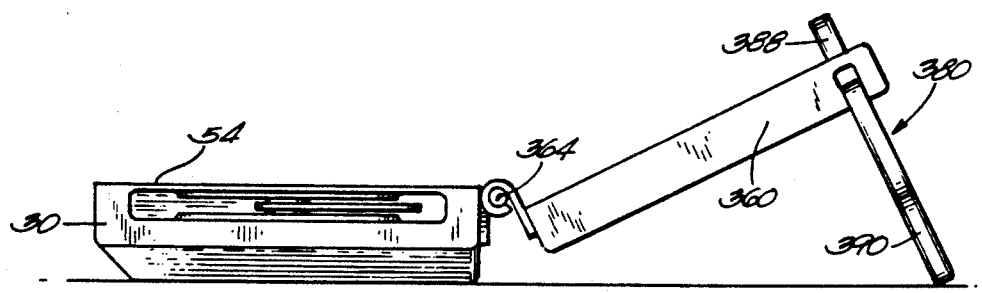
FIG. 34 is a view similar to FIG. 33 showing the cover in its open position and supported by the latching members.

The cover 360 is preferably made of plastic and is movable relative to the base 30 between an open position (shown in FIG. 34) and a closed position (shown in FIG. 32). The cover 360 has an inner surface 368 which engages the upper surface 54 of the base 30 when the cover 360 is in its closed position. The cover 360 has therein (see FIGS. 16 and 32) a generally rectangular access opening 372 affording access to the top plate 250 when the cover 360 is in its closed position.

Figure 27:
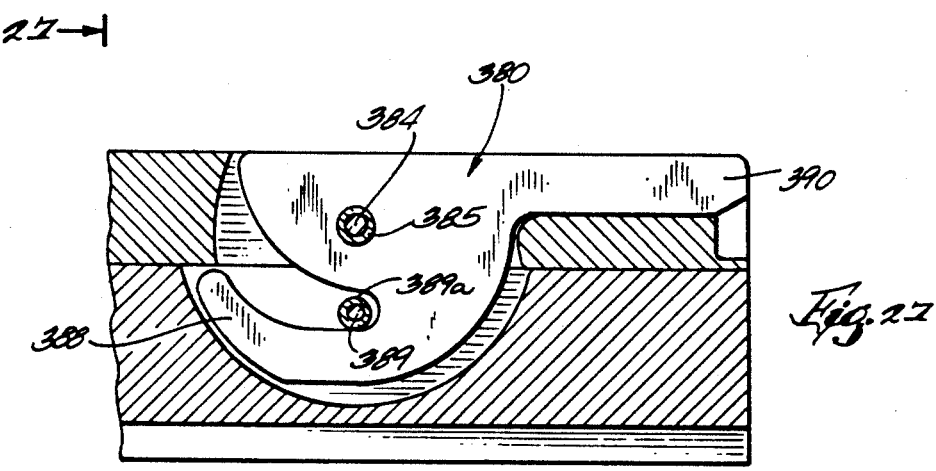
FIG. 27 is a view taken along line 27—27 in FIG. 26.
Figures 28, 29, 38:
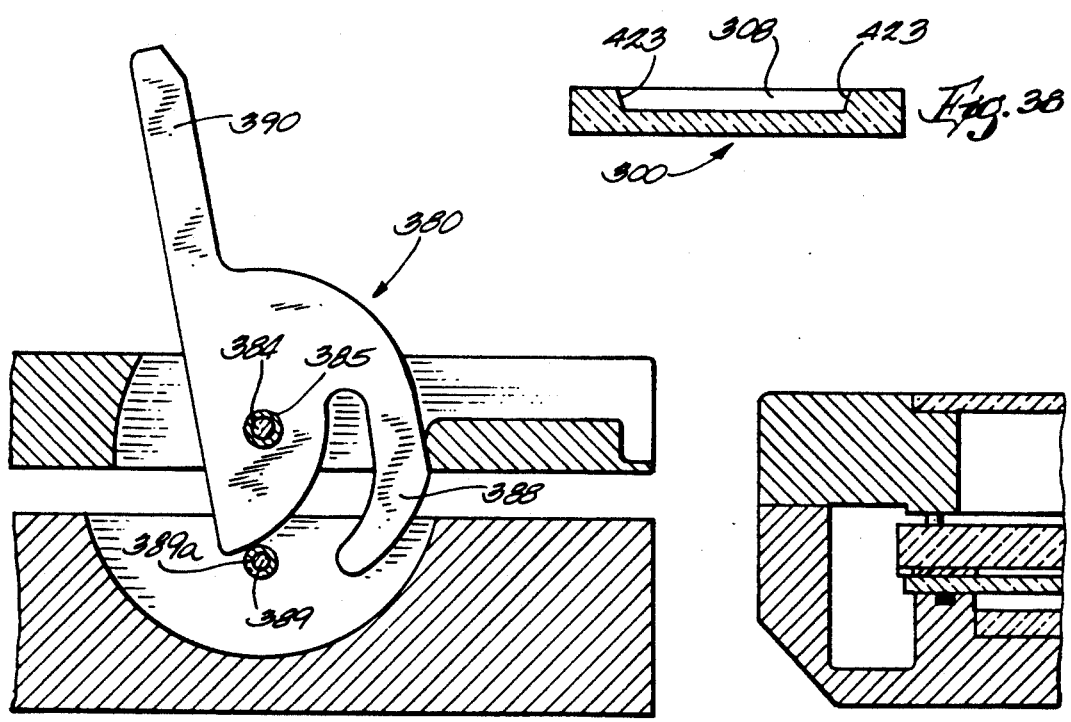
FIG. 28 is a view similar to FIG. 27 showing a latching member in its released position.
FIG. 29 is a view taken along line 29—29 in FIG. 16.
FIG. 38 is a view taken along line 38—38 in FIG. 12.

Means are provided for releasably retaining the cover 360 in its closed position. Such means preferably includes (see FIGS. 27, 28, 33 and 34) a pair of latch members 380. Each of the members 380 is mounted on the cover 360 for movement relative thereto between a latching position (shown in FIG. 27) and a released position (shown in FIG. 28). Each of the latch members 380 is pivotally mounted on (see FIG. 27) a pin 384 supported by the cover 360, with a bearing 385 between the pin 384 and the member 380, and each latch member includes a hook portion 388 which engages an associated pin 389 (surrounded by bearing 389a) supported by the base 30 when the latch member 380 is in its latching position. The hook portion 388 disengages the base pin 389 when the latch member 380 is moved to its released position. Each latch member 380 includes a handle portion 390 which provides a leg supporting the cover 360 when the cover 360 is in its open position and the latch member 380 is in its released position.

Means are provided on the cover 360 for biasing the cathode block 260, the top plate 250 and the anode block 300 downwardly and against the upper surface 224 of the gasket 220 when the cover 360 is in its closed position. The biasing means includes (see FIG. 16) two biasing mechanisms 391 that bias the cathode block 260 downwardly, two biasing mechanisms 392 that bias the anode block 300 downwardly, and ten biasing mechanisms 393 that bias the top plate 250 downwardly. One biasing mechanism 391, one biasing mechanism 392, and five biasing mechanisms 393 are located in the cover 360 in front of the access opening 372, and one biasing mechanism 391, one biasing mechanism 392, and five biasing mechanisms 393 are located in the cover 360 rearwardly of the access opening 372. The biasing mechanisms 391, 392 and 393 are substantially identical, and only one of the mechanisms 393 will be described in detail.

The biasing mechanism 393 includes (see FIG. 25) a plunger 394 which includes a reduced-diameter portion 394a and an enlarged-diameter portion 394b slidably housed in a bore 395 in the cover 360. The reduced-diameter portion 394a extends through a bore 396 in a wall 397 having an upper surface 397a defining the lower end of the bore 395 and having a lower surface partially defining the inner or lower surface 368 of the cover 360. The enlarged-diameter portion 394b engages the wall 397 so as to limit downward movement of the plunger 394 relative to the cover 360. The biasing means also includes a plug 398 threaded into the upper end of the bore 395. The upper end of the plug 398 has therein a socket 398a that receives a suitable tool, such as an Allen wrench, so that the plug 398 can be threaded into and out of the bore 395. The biasing means also includes a spring 399 extending between the plug 398 and the enlarged-diameter portion 394b of the plunger 394 so as to bias the plunger 394 downwardly relative to the cover 360. Adjustment of the position of the plug 398 in the bore 395 adjusts the force exerted on the plunger 394 by the spring 399.

When the cover 360 is open, no downward force is exerted on the cathode block 260, the top plate 250 and the anode block 300, and these components can be removed from the base 30. The springs 399 of the mechanisms 391, 392 and 393 push the plungers 394 downwardly such that the enlarged-diameter portions 394b of the plungers 394 engage the upper surface 397a of the walls 397. When the cover 360 is closed, the plungers 394 of the mechanisms 391 engage the cathode block 260, the plungers 394 of the mechanisms 393 engage the top plate 250, and the plungers 394 of the mechanisms 392 engage the anode block 300. Such engagement of the cathode block 260, the top plate 250 and the anode block 300 causes upward movement of the plungers 394 relative to the cover 360 and against the forces of the springs 399. The springs 399 thus exert, through the plungers 394, downward forces on the cathode block 260, the top plate 250 and the anode block 300. The biasing means is user adjustable and exerts a controlled force on the cathode block 260, the top plate 250 and the anode block 300.

Figure 30:
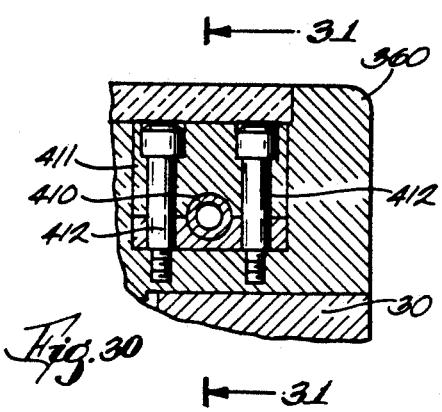
FIG. 30 is a view taken along line 30—30 in FIG. 21.
Figure 31:
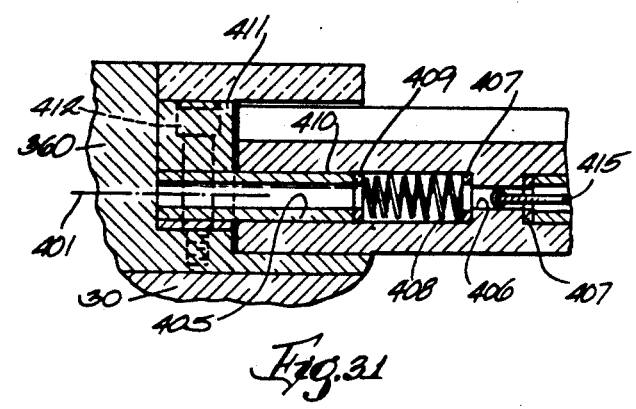
FIG. 31 is a view taken along line 31—31 in FIG. 30.

The cell 12 further comprises (see FIGS. 21-24, 30, 31, 37, 39 and 40) an anode electrode 400 mounted on the cover 360. The electrode 400 pivots about an axis 401 perpendicular to the axis 364. The electrode 400 is a block of solid material, preferably plastic, having opposite front and rear end surfaces 402 and 403 and an electrode surface 404 extending between the end surfaces. Each of the end surfaces 402 and 403 has therein a substantially blind bore 405 centered on the axis 401. The blind ends of the bores 405 are connected by a smaller through bore 406. Located in each of the bores 405 are (see FIGS. 31 and 37), in order from the inner end of the bore to the outer end of the bore, a washer 407, a spring 408, a washer 409, and a sleeve 410 extending partially outside of the bore 405. As best shown in FIGS. 30 and 31, the outer end of each sleeve 410 is captured between upper and lower portions of an associated bearing block 411 secured to the cover 360 by screws 412. The bearing blocks 411 hold the sleeves 410 against rotation, and the electrode 400 rotates about the sleeves 410 and thus about the axis 401. The springs 408, acting through the washers 409 and the sleeves 410, bias the electrode 400 to a center position relative to the cover 360, but the springs 408 allow axial movement (up and down in FIG. 16) of the electrode 400 relative to the cover 360.

Press fit in the outer end of the rear sleeve 410 (the upper sleeve in FIG. 21) is a conductive pin or connector 413 (FIGS. 21 and 37). The outer end of the connector 413 is received by a conventional female electrical connector 414 supported by the cover 360. A conductive wire 415 (FIGS. 24 and 31) has one end electrically connected to the inner end of the connector 413 by suitable means such as soldering. The wire 415 extends through the rear sleeve 410 and the associated washer 409, spring 408, and washer 407, through a portion of the small bore 406 and then through a generally L-shaped passageway 416 extending from the small bore 406 to the front end surface 402. A set screw 417 threaded into the electrode 400 secures the wire 415 in the passageway 416. From the front end surface 402 the wire 415 extends across the electrode surface 404 to the rear end surface 403. The electrode surface 404 preferably has therein a groove 404a (FIG. 39) in which the wire 415 is seated. From the rear end surface 403 the wire 415 extends into a short passageway 418, and a set screw 419 secures the end of the wire 415 in the passageway 418. The screws 417 and 419 maintain tension in wire 415 across surface 404.

The electrode 400 is pivotal relative to the cover 360 between a down position (shown in FIG. 22) and an up position (shown in FIG. 23). In the up position, the electrode 400 is removed from the buffer chamber 308 when the cover 360 is in its closed position. When the cover 360 is in its closed position and the electrode 400 is in its down position, the electrode 400 is in an engaged position wherein the electrode 400 extends into the buffer chamber 308 and the portion of the wire extending across the electrode surface is located in the buffer chamber 308. The electrode 400 can be moved to the engaged position either by closing the cover 360 with the electrode 400 in its down position or by moving the electrode 400 from its up position to its down position when the cover 360 is in its closed position.

The cell 12 further comprises (see FIG. 16) a cathode electrode 420 mounted on the cover 360 for pivotal movement relative thereto between a down position (shown in FIG. 16) and an up position (not shown). The electrode 420 is substantially identical to the electrode 400 and therefore will not be described in detail. The electrode 420 pivots about an axis 421 (FIG. 16) perpendicular to the axis 364 and parallel to the axis 401, and the electrode 420 is movable along its pivot axis 421 and is biased to a center position. In the up position, the electrode 420 is removed from the buffer chamber 268 when the cover 360 is in its closed position. When the cover 360 is in its closed position and the electrode 420 is in its down position, the electrode 420 is in an engaged position wherein the electrode extends into the buffer chamber 268. The electrode 420 can be moved to the engaged position either by closing the cover 360 with the electrode 420 in its down position or by moving the electrode 420 from its up position to its down position when the cover 360 is in its closed position.

In the illustrated embodiment, means are provided for aligning each of the electrodes 400 and 420 relative to its respective buffer chamber 308 or 268 in response to movement of the electrode to its engaged position. Such means preferably includes (see FIGS. 24 and 38) interengaging ramped surfaces 422 and 423 on the anode electrode 400 and the anode block 300, respectively, and substantially identical interengaging ramped surfaces (not shown) on the cathode electrode 420 and the cathode block 260. When either of the electrodes 400 or 420 is moved to its engaged position, the ramped surfaces 422 and 423 will guide the electrode into the center of the respective buffer chamber 308 or 268. The springs 408 allow movement of the electrode relative to the cover 360 to accommodate movement of the electrode relative to the respective buffer chamber.

The access opening 372 provides access to the electrodes 400 and 420 and allows a user to move the electrodes 400 and 420 between their up and down positions when the cover 360 is closed. As shown in FIGS. 1, 32 and 35, an access door or lid 425 is mounted on the cover 360 for pivotal movement relative thereto about a generally horizontal axis 426 (FIGS. 16 and 35) parallel to the base axis 34. The lid 425 is preferably connected to the cover 360 by conventional hinges 427. The lid 425 is movable relative to the cover 360 between an open position (shown partially open in FIG. 36) wherein the lid affords access to the access opening 372, and a closed position (shown in FIG. 35) wherein the lid 425 closes the access opening 372. Two conventional push-button latches 430 (see FIGS. 16, 35 and 36) releasably secure the lid 425 in its closed position. The lid 425 is preferably made of transparent plastic so that the interior of the cell 12 is visible therethrough.

The cell 12 further comprises (see FIGS. 16-18) electrical connector means 450 mounted on the cover 360. The connector means 450 includes a terminal 454 electrically connected to the connector 414 of the cathode electrode 420 and a terminal 458 electrically connected to the connector 414 of the anode electrode 400. The cell 12 further comprises electrical connector means 460 selectively engageable with the connector means 450. The connector means 460 is connected to the power supply 16 and includes a connector member 461 that slides downwardly into a complementary slot 462 in the cover 360 and in the base 30 in order to engage the connector means 450 and 460. As shown in FIG. 17, the slot 462 has rearwardly converging side walls that prevent rearward removal of the member 461 from the slot 462. Thus, the member 461 can only be removed from the slot 462 by upward movement of the member 461. As also shown in FIGS. 17 and 18, a portion 463 of the member 461 extends rearwardly of the cover 360 and of the base 30. The connector member 461 supports terminals 464 and 468 which are electrically connected to the terminals 454 and 458, respectively, when the connector means 450 and 460 are engaged. Thus, engagement of the connector means 450 and 460 electrically connects the electrodes 400 and 420, and particularly the wires 415 of the electrodes, to the power supply 16.

Interlock means are provided for preventing opening of the lid 425 and the cover 360 when the connector means 450 and 460 are engaged and for preventing the connector means 450 and 460 from being engaged when either the lid 425 or the cover 360 is open. The interlock means preferably includes the portion 463 of the connector member 461 and the interengagement of the member 461 and the slot 462. When the connector means 450 and 460 are engaged, the engagement of the cover 360 and the base 30 by the member 461 in the slot 462 interferes with opening of the cover 360. If the user attempts to engage the connector means 450 and 460 when the cover 360 is open, the rear surface of the base 30 interferes with the portion 463 of the member 461, and such interference prevents engagement of the connector means 450 and 460.

The interlock means also includes (see FIG. 18) a forward portion 484 of the connector member 461. When the lid 425 is closed, the connector portion 484 extends over the lid 425 and interferes with movement of the lid 425 from its closed position. If the user attempts to engage the connector means 450 and 460 when the lid 425 is fully open, the lid 425 interferes with the connector means 460, and such interference prevents engagement of the connector means 450 and 460.

The sequencing cell operates as follows. With the cover 360 open, the bottom plate 190 is seated on the O-ring 184 and the gasket 220 is seated on the upper surface of the bottom plate 190. Next the top plate 250 is seated on the gasket 220 with the top plate end surface 258 against the base walls 118 and 126. Then the anode block 300 is seated on top of the gasket 220, with the anode gaskets 310 between the anode block 300 and the top plate 250, and the cam member 344 is moved to its biasing position. Next the cathode block 260 is seated on top of the gasket 220, with the cathode gaskets 280 between the cathode block 260 and the top plate 250. The comb 290 is then placed in the gap 266, and the cam member 324 is moved to its biasing position. Next, the cover 360 is closed and the latch members 380 are moved to their latching positions. Closing of the cover 360 causes the biasing means 391, 392 and 393 to push the cathode block 260, the top plate 250 and the anode block 300 downwardly against the gasket 220, thus sealing the gel space 254 and the water jacket 82 (by pushing the bottom plate 190 against the O-ring 184). The cover 360 can be closed with the electrodes 400 and 420 in either their up positions or their down positions. If the cover 360 is closed with the electrodes 400 and 420 in their down positions, the electrodes should be moved to their up positions before the following steps. The lid 425 must be open in order to move the electrodes to their up positions.

Next, gel-forming liquid is introduced into the cathode buffer chamber 268 and allowed to flow into the gel space 254. The liquid should fill the gel space 254 and flow into the gaps 266 and 306. The comb 290 is removed after the gel polymerizes, leaving sample wells in the gel. The electrodes 400 and 420 are then moved to their down positions, and thereby to their engaged positions (because the cover 360 is closed). A small amount of buffer solution is then introduced into each buffer chamber 268 and 308. The buffer solution is also squirted into the sample wells to remove residual gel-forming liquid and urea. Samples are loaded into the sample wells as is known in the art. The water inlet 160 and water outlet 140 are connected to the temperature regulator 14, and water is circulated through the water jacket 82.

Finally, the lid 425 is closed and the connector means 460 is engaged with the connector means 450, thereby electrically connecting the electrodes to the power supply 16.

Various features of the invention are set forth in the following claims.

We claim:

1. Electrophoresis apparatus comprising:
   a base including a water jacket having opposite first and second ends, water outlet means communicating with said second end of said water jacket, and water inlet means communicating with said first end of said water jacket, said water inlet means including a main water inlet passage extending in spaced relation to said first end of said water jacket, said main passage including a first portion having a first cross-sectional area, and a second portion which is downstream of said first portion and which has a second cross-sectional area less than said first cross-sectional area, and said water inlet means also including a first passageway which extends between said first portion and said water jacket, and a second passageway which extends between said second portion and said water jacket.
   an inner plate having an outer surface, and an inner surface which is supported by said base and which extends over said water jacket,
   an endless gasket having an inner surface engaging said outer surface of said inner plate, and having an outer surface,
   an outer plate having an inner surface seated on said outer surface of said gasket so as to define between said plates and inside said gasket a space adapted to contain a separation medium,
   means defining first and second buffer chambers communicating with said space, and
   first and second electrodes which are extendable into said first and second buffer chambers, respectively, and which are adapted to apply an electric field to the separation medium.

2. Apparatus as set forth in claim 1 wherein said first passageway has a cross-sectional area, and wherein said second passageway has a cross-sectional area greater than said cross-sectional area of said first passageway.

3. Apparatus as set forth in claim 2 wherein said passage also includes a third portion which is downstream of said second portion and which has a third cross-sectional area less than said second cross-sectional area, and a fourth portion which is downstream of said third portion and which has a fourth cross-sectional area less than said third cross-sectional area, and wherein said water inlet means also includes a third passageway which extends between said third portion and said water jacket and which has a cross-sectional area greater than said cross-sectional area of said second passageway, and a fourth passageway which extends between said fourth portion and said water jacket and which has a cross-sectional area substantially equal to said cross-sectional area of said third passageway.

4. Apparatus as set forth in claim 3 wherein said main passage and said first, second, third and fourth passageways extend generally horizontally, wherein said water jacket extends generally horizontally from said first end to said second end and has opposite sides extending between said first and second ends, and wherein said first, second, third and fourth passageways are spaced horizontally between said opposite sides of said water jacket.

5. Apparatus as set forth in claim 1 wherein said base also includes an upwardly facing plate seating surface surrounding said water jacket and having therein an endless O-ring channel, wherein said apparatus further comprises an O-ring located in said O-ring channel, wherein said inner plate extends generally horizontally and is seated on said O-ring, and wherein said outer plate extends generally horizontally.

6. Electrophoresis apparatus comprising
   a base including a water jacket,
   an inner plate having a periphery, an outer surface, and an inner surface which is supported by said base and which extends over said water jacket,
   an endless gasket having an inner surface engaging said outer surface of said inner plate, an outer surface, and a portion spaced inwardly from said periphery of said inner plate so as to provide a space between said gasket and said periphery of said inner plate,
   an outer plate having an inner surface seated on said outer surface of said gasket so as to define between said plates and inside said gasket a space adapted to contain a separation medium,
   means defining first and second buffer chambers communicating with said space, and
   first and second electrodes which are extendable into said first and second buffer chambers, respectively, and which are adapted to apply an electric field to the separation medium.

7. Apparatus as set forth in claim 6 wherein said inner plate includes opposite ends and opposite sides extending between said ends, wherein said gasket includes opposite end segments located adjacent said ends of said inner plate, and opposite side segments each located adjacent a respective one of said opposite sides of said inner plate, and wherein said side segments are spaced inwardly from said sides of said inner plate.

8. Apparatus as set forth in claim 7 wherein said end segments are spaced inwardly from said end of said inner plate.

9. Apparatus as set forth in claim 7 wherein each of said side segments includes opposite end portions and an indented portion which extends between said end portions and which is indented so as to be spaced from the associated side of said inner plate.

10. Apparatus as set forth in claim 6 wherein said base also includes an upwardly facing plate seating surface surrounding said water jacket and having therein an endless O-ring channel, wherein said apparatus further comprises an O-ring located in said O-ring channel, wherein said inner plate extends generally horizontally and is seated on said O-ring, and wherein said outer plate extends generally horizontally.

11. Apparatus as set forth in claim 10 wherein said plate seating surface has therein a first elongated well extending beneath one of said sides of said inner plate on the opposite side of said O-ring relative to said water jacket, and a second elongated well extending beneath the other of said sides of said inner plate on the opposite side of said O-ring relative to said water jacket.

12. Electrophoresis apparatus comprising:
a base including a water jacket,
an inner plate having opposite ends, opposite sides extending between said ends, an outer surface, and an inner surface which is supported by said base and which extends over said water jacket,
an endless gasket having an inner surface engaging said outer surface of said inner plate, an outer surface, opposite end segments located adjacent said ends of said inner plate, and opposite side segments each located adjacent a respective one of said opposite sides of said inner plate, and each including an interior surface which extends between said inner and outer surfaces of said gasket and which has therein an indentation adjacent each of said end segments,
an outer plate having an inner surface seated on said outer surface of said gasket so as to define between said plates and inside said gasket a space adapted to contain a separation medium,
means defining first and second buffer chambers communicating with said space, and
first and second electrodes which are extendable into said first and second buffer chambers, respectively, and which are adapted to apply an electric field to the separation medium.

13. Apparatus as set forth in claim 12 wherein said base also include an upwardly facing plate seating surface surrounding said water jacket and having therein an endless O-ring channel, wherein said apparatus further comprises an O-ring located in said O-ring channel, wherein said inner plate extends generally horizontally and is seated on said O-ring, and wherein, said outer plate extends generally horizontally.

14. Apparatus as set forth in claim 12 wherein each of said side segments is spaced inwardly from said opposite sides of said inner plate.

15. Apparatus as set forth in claim 12 wherein said interior surface of each of said side segments includes a generally linear main portion and a ramped transition between each of said indentations and said main portion.

16. Electrophoresis apparatus comprising
a base including generally vertically entering walls, a water jacket having opposite sides, and an upwardly facing plate seating surface surrounding said water jacket and having therein an endless O-ring channel, a first elongated well on one side of said water jacket, and a second elongated well on the opposite side of said water jacket, each of said wells having opposite ends, each of said opposite ends of said wells being defined by a respective one of said vertically extending walls of said base,
an O-ring located in said O-ring channel,
a generally horizontal bottom plate having an upper surface, opposite sides, and a lower surface which is seated on said O-ring and which extends over said water jacket, said first well extending beneath one of said sides of said bottom plate, and said second well extending beneath the other of said sides of said bottom plate,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium, and said top plate having opposite ends engaged by said vertical walls of said base so that said walls limit movement of said top plate relative to said base,
means defining first and second buffer chambers communicating with said space, and
first and second electrodes which are extendable into said first and second buffer chambers, respectively, and which are adapted to apply an electric field to the separation medium.

17. Electrophoresis apparatus comprising
a base including a water jacket having opposite sides, and an upwardly facing plate seating surface which surrounds said water jacket and which has therein an endless O-ring channel, a first elongated well extending along one of sad sides of said water jacket on the opposite side of sad O-ring channel relative to said water jacket, and a second elongated well extending along the other of said sides of said water jacket on the opposite side of said O-ring channel relative to said water jacket,
an O-ring located in said O-ring channel,
a generally horizontal bottom plate having a first side extending above said first well, a second side extending above said second well, an upper surface, and a lower surface seated on said O-ring,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
means defining first and second buffer chambers communicating with said space, and
first and second electrodes which are extendable into said first and second buffer chambers, respectively, and which are adapted to apply an electric field to the separation medium.

18. Electrophoresis apparatus comprising
a base including a water jacket,
a generally horizontal bottom plate having an upper surface, and a lower surface which is supported by said base and which extends over sad water jacket, an endless gasket having opposite first and second side segments, having a lower surface engaging said upper surface of said bottom pate, and having an upper surface, a generally horizontal top plate having an upper surface, having an end surface, and having a lower surface seated on said upper surface of said gasket so as to define between said plates and inside said gasket a spaced adapted to contain a separation medium, a cathode block having a substantially planar lower surface seated on said upper surface of said gasket, said cathode block having a generally vertical end surface spaced from said end surface of said top plate so as to form therebetween a gap, a first cathode gasket which is located in said gap and which sealingly engages said cathode block end surface, said top plate end surface, and said first gasket segment, said first cathode gasket being U-shaped and opening upwardly, a second cathode gasket which is located in said gap and which sealingly engages said cathode block end surface, said top plate end surface, and said second gasket segment, said second cathode gasket being U-shaped and opening upwardly, means defining first and second buffer chambers communicating with said space, said means defining said first buffer chamber including sad cathode block, and first and second electrodes which are extendable into said first and second buffer chambers, respectively, and which are adapted to apply an electric field to the separation medium.

19. Apparatus as set forth in claim 18 wherein said cathode block end surface has therein first and second U-shaped recesses respectively housing said first and second cathode gaskets.

20. Electrophoresis apparatus comprising a base including a water jacket, a generally horizontal bottom plate having an upper surface, and a lower surface which is supported by said base and which extends over said water jacket, an endless gasket having opposite first and second side segments, having a lower surface engaging said upper surface of said bottom plate, and having an upper surface, a generally horizontal top plate having an end surface, and having a lower surface seated on said upper surface of said gasket so as to define between said plates and inside said gasket a space adapted to contain a separation medium, a cathode block having a substantially planar lower surface seated on said upper surface of said gasket, said cathode block having a generally vertical end surface spaced from said end surface of said top plate so as to form therebetween a gap communicating with said space, a first cathode gasket which is located in said gap and which sealingly engages said cathode block end surface, said top plate end surface, and said first gasket segment, a second cathode gasket which is located in said gap and which sealingly engages said cathode block end surface, said top plate end surface, and said second gasket segment, cam means for biasing said cathode block end surface toward said top plate end surface, said cam means including a pivot pin which extends generally vertically and which is supported by said base, a cam member pivotally mounted on said pivot pin, and a resilient bushing between said cam member and said pivot pin, said cam member being movable between a biasing position wherein said cam member engages said cathode block so as to bias said cathode block toward said top plate, so as to compress said cathode gaskets between said cathode block and said top plate, and so as to compress said bushing between said first cam member and said pivot pin, and a non-biasing position wherein said cam member does not exert a force on said cathode block, means defining first and second buffer chambers communicating with said space, said means defining said first buffer chamber including said cathode block, and first and second electrodes which are extendable into said first and second buffer chambers, respectively, and which are adapted to apply an electric field to the separation medium.

21. Apparatus as set forth in claim 20 wherein said top plate has a second end surface opposite said first end surface, and wherein said apparatus further comprises an anode block having a substantially planar lower surface seated on said upper surface of said gasket, said anode block having a generally vertical end surface spaced from said second end surface of said top plate so as to form therebetween a second gap communicating with said space, a first anode gasket which is located in said second gap and which sealingly engages said anode block end surface, said second top plate end surface, and said first gasket segment, a second anode gasket which is located in said second gap and which sealingly engages said anode block end surface, said second top plate end surface, and said second gasket segment, and second cam means for biasing said anode block end surface toward said second top plate end surface, said second cam means including a second pivot pin which extends generally vertically and which is supported by said base, a second cam member pivotally mounted on said second pivot pin, and a second resilient bushing between said second cam member and said second pivot pin, said second cam member being movable between a biasing position wherein said second cam member engages said anode block so as to bias said anode block toward said top plate, so as to compress said anode gaskets between said anode block and said top plate, and so as to compress said second bushing between said second cam member and said second pivot pin, and a non-biasing position wherein said second cam member does not exert a force on said anode block.

22. Apparatus as set forth in claim 21 wherein the force exerted on one of said cathode block and said anode block by the associated cam member is greater than the force exerted on the other of said cathode block and said anode block by the associated cam member.

23. Electrophoresis apparatus comprising a base including a water jacket, a generally horizontal bottom plate having an upper surface, and a lower surface which is supported by said base and which extends over said water jacket, an endless gasket having a lower surface engaging said upper surface of said bottom plate, and having an upper surface, a generally horizontal top plate having opposite first and second end surfaces, and having a lower surface seated on said upper surface of said gasket so as to define between said plates and inside said gasket a space adapted to contain a separation medium, a cathode block having a substantially planar lower surface seated on aid upper surface of said gasket, said cathode block having a generally vertical end surface spaced from said first end surface of said top plate so as to form therebetween a gap, a first cathode gasket which is located in said gap and which sealingly engages said cathode block end surface, said first top plate end surface, and said first gasket segment, a second cathode gasket which is located in said gap and which sealingly engages said cathode block end surface, said first top plate end surface, and said second gasket segment, first cam means for biasing said cathode block end surface toward said top plate first end surface, an anode block having a substantially planer lower surface seated on said upper surface of said gasket, said anode block having a generally vertical end surface spaced from said second end surface of said top plate so as to form therebetween a second gap communicating with said space, a first anode gasket which is located in said second gap and which sealingly engages said anode block end surface, said second top plate end surface, and said first gasket segment, a second anode gasket which is located in said second gap and which sealingly engages said anode block end surface, said second top plate end surface, and said second gasket segment, second cam means for biasing said anode block end surface toward said second top plate end surface, the force exerted on one of said cathode block and said anode block by the associated cam member being greater than the force exerted on the other of said cathode block and said anode block by the associated cam member, means including said cathode block and said anode block for defining first and second buffer chambers communicating with said space, and first and second electrodes which are extendable into said first and second buffer chambers, respectively, and which are adapted to apply an electric field to the separation medium.

24. Electrophoresis apparatus comprising
a base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
a cover mounted on said base for pivotal movement relative thereto about a generally horizontal axis, said cover being movable relative to said base between an open position and a closed position, and said cover including an inner surface which engages said upper surface of said base when said cover is in said closed position;

means defining first and second buffer chambers communicating with said space, and
first and second electrodes which are extendable into said first and second buffer chambers, respectively, and which are adapted to apply an electric field to the separation medium.

25. Apparatus as set forth in claim 24 wherein said electrodes are mounted on said cover.

26. Electrophoresis apparatus comprising
a base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
a cover including an inner surface which engages said upper surface of said base when said cover is in a closed position,
means on said cover for biasing said top plate downwardly and against said upper surface of said gasket when said cover is in said closed position,
means defining first and second buffer chambers communicating with said space, and
first and second electrodes which are extendable into said first and second buffer chambers, respectively, and which are adapted to apply an electric field to he separation medium.

27. Apparatus as set forth in claim 26 wherein said biasing means is user adjustable.

28. Apparatus as set forth in claim 26 wherein said cover is mounted on said base for pivotal movement relative thereto about a generally horizontal axis and between an open position and said closed position.

29. Apparatus as set forth in claim 26 wherein said electrodes are mounted on said cover.

30. Electrophoresis apparatus comprising
a base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
a cover including an inner surface which engages said upper surface of said base when said cover is in a closed position, and said cover having therein an access opening,
an access door mounted on said cover for movement relative thereto between an open position wherein said access door affords access to said access opening, and a closed position wherein said access door covers said access opening,
means defining first and second buffer chambers communicating with said space, and
first and second electrodes which are extendable into said first and second buffer chambers, respectively, and which are adapted to apply an electric field to the separation medium.

31. Apparatus as set forth in claim 30 wherein said cover is mounted on said base for pivotal movement relative thereto about a generally horizontal axis and between an open position and said closed position.

32. Apparatus as set forth in claim 31 and further comprising means on said cover for biasing said top plate downwardly and against said upper surface of said gasket when said cover is in said closed position.

33. Apparatus as set forth in claim 30 wherein said electrodes are mounted on said cover.

34. Electrophoresis apparatus comprising
a base adapted to sit on a supporting surface, said base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
a cover including an inner surface which engages said upper surface of said base when said cover is in a closed position,
means for releasably retaining said cover in said closed position, said retaining means including a latch member which is mounted on said cover for movement relative thereto between a latching position and a released position, said latch member including a handle portion adapted to engage the supporting surface so as to support said cover above the supporting surface when said cover is in said open position and said latch member is in said released position,
means defining first and second buffer chambers communicating with said space, and
first and second electrodes which are extendable into said first and second buffer chambers, respectively, and which are adapted to apply an electric field to the separation medium.

35. Apparatus as set forth in claim 34 wherein said cover is mounted on said base for pivotal movement relative thereto about a generally horizontal axis and between an open position and said closed position.

36. Apparatus as set forth in claim 35 and further comprising means on said cover for biasing said top plate downwardly and against said upper surface of said gasket when said cover is in said closed position.

37. Apparatus as set forth in claim 36 wherein said cover has therein an access opening, and wherein said apparatus further comprises an access door mounted on said cover for movement relative thereto between an open position wherein said access door affords access to said access opening, and a closed position wherein said access door covers said access opening.

38. Apparatus as set forth in claim 34 wherein said electrodes are mounted on said cover.

39. Electrophoresis apparatus comprising
a base including a water jacket, and an upper surface,
a generally horizontal bottom plate having an upper surface and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium;
means defining first and second buffer chambers communicating with said space,
a cover mounted on said base for movement relative thereto between an open position and a closed position, said cover including an inner surface which engages said upper surface of said base when said cover is in a closed position,
a first electrode which is supported by said cover and which is extendable into said first buffer chamber when said cover is in said closed position,
a second electrode which is supported by said cover and which is extendable into said second buffer chamber when said cover is in said closed position,
first electrical connector means mounted on said cover and electrically connected to said first electrode,
second electrical connector means which is adapted to be connected to a source of power and which is selectively engageable with said first electrical connector means, and
interlock means for preventing opening of said cover when said second connector means is connected to said first connector means, and for preventing said second connector means from being connected to said first connector means when said cover is open.

40. Apparatus as set forth in claim 39 wherein said cover has therein an access opening, wherein said apparatus further comprises an access door mounted on said cover for movement relative thereto between an open position wherein said access door affords access to said access opening, and a closed position wherein said access door covers said access opening, and wherein said interlock means also prevents opening of said access door when said second connector means is connected to said first connector means, and prevents said second connector means from being connected to said first connector means when said access door is open.

41. Electrophoroesis apparatus comprising
a base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium,
means defining first and second buffer chambers communicating with said space,
a cover mounted on said base for movement relative thereto between an open position and a closed position, said cover including an inner surface which engages said upper surface of said base when said cover is in a closed position,
a first electrode mounted on said cover for movement relative thereto between a down position wherein said first electrode extends into a said first buffer chamber when said cover is in said closed position, and an up position wherein said first electrode is removed from said first buffer chamber when said cover is in said closed position, and a second electrode mounted on said cover for movement relative thereto between a down position wherein said second electrode extends into said second buffer chamber when said cover is in said closed position, and an up position wherein said second electrode is removed from said second buffer chamber when said cover is in said closed position, and said second electrode being adapted to cooperate with said first electrode to apply an electric field to the separation medium.

42. Apparatus as set forth in claim 41 and further comprising first electrical connector means mounted on said cover and electrically connected to said electrode, second electrical connector means which is adapted to be connected to a source of power and which is selectively engageable with said first electrical connector means, and interlock means for preventing opening of said cover when said second connector means is connected to said first connector means, and for preventing said second connector means from being connected to said first connector means when said cover is open.

43. Electrophoresis apparatus comprising
a base including a water jacket, and an upper surface,
a generally horizontal bottom plate having an upper surface, and a lower surface which is supported by said base and which extends over said water jacket,
an endless gasket having a lower surface engaging said upper surface of said bottom plate, and having an upper surface,
a generally horizontal top plate having a lower surface seated on said upper surface of said gasket so as to define between said plates and inside said gasket a space adapted to contain a separation medium;
means defining first and second buffer chambers communicating with said space,
a first electrode movable relative to an engaged position wherein said first electrode extends into said first buffer chamber,
means for automatically aligning said first electrode relative to said first buffer chamber in response to movement of said first electrode to said engaged position, and
a second electrode which is movable relative to an engaged position wherein said second electode extends into said second buffer chamber and which is adapted to cooperate with said first electrode to apply an electric field to the separation medium.

44. Apparatus as set forth in claim 43 and further comprising a cover mounted on said base for movement relative thereto between an open position and a closed position, said cover including an inner surface which engages said upper surface of said base when said cover is in a closed position, and wherein said electrode is movable to said engaged position by movement of said cover to said closed position.

45. Apparatus as set forth in claim 44 wherein said electrode is mounted on said cover for movement relative thereto between a down position wherein said electrode is in said engaged position when said cover is in said closed position, and an up position wherein said electrode is removed from said buffer chamber when said cover is in said closed position, and wherein said electrode is movable to said engaged position by movement of said electrode from said up position to said down position when said cover is in said closed position.

46. Apparatus as set forth in claim 43 wherein said aligning means includes ramped surfaces on at least one of said electrode and said chamber defining means.

47. Apparatus as set forth in claim 41 wherein said second electrode is movable relative to an engaged position wherein said second electrode extends into said second buffer chamber, and wherein sad apparatus further comprises means for automatically aligning said second electrode relative to said second buffer chamber in response to movement of said second electrode to said engaged position.

48. Electrophoresis apparatus comprising
a base including a water jacket having upstream and downstream ends and having a decreased cross-sectional area at a point downstream of said upstream end, water inlet means communicating with said upstream end of said water jackets, and water outlet means communicating with said downstream end of said water jacket,
an inter plate having an outer surface, and an inner surface which is supported by said base and which extends over said water jacket,
an endless gasket having an inner surface engaging said outer surface of said bottom plate, and having an outer surface,
an outer plate having an inner surface seated on said outer surface of said gasket so as to define between said plates and inside said gasket a space adapted to contain a separation medium,
means defining first and second buffer chambers communicating with said space, and
first and second electrodes which are extendable into said first and second buffer chambers, respectively, and which are adapted to apply an electric field to the separation medium.

49. Apparatus as set forth in claim 48 wherein said base includes a water jacket cavity partially defining said water jacket, and wherein said cavity has therein an insert creating said decreased cross-sectional area.

* * * * *